(12) United States Patent
Itu et al.

(10) Patent No.: US 11,847,779 B2
(45) Date of Patent: Dec. 19, 2023

(54) CLINICAL DECISION SUPPORT FOR CARDIOVASCULAR DISEASE BASED ON A PLURALITY OF MEDICAL ASSESSMENTS

(71) Applicant: Siemens Healthcare GmbH, Erlangen (DE)

(72) Inventors: Lucian Mihai Itu, Brasov (RO); Puneet Sharma, Princeton Junction, NJ (US); Ulrich Hartung, Langensendelbach (DE); Catalin Lungu, Brasov (RO)

(73) Assignee: Siemens Healthcare GmbH, Erlangen (DE)

(*) Notice: Subject to any disclaimer, the term of this patent is extended or adjusted under 35 U.S.C. 154(b) by 418 days.

(21) Appl. No.: 17/304,746

(22) Filed: Jun. 25, 2021

(65) Prior Publication Data

US 2022/0414865 A1 Dec. 29, 2022

(51) Int. Cl.
*G06T 7/00* (2017.01)
*G06T 7/11* (2017.01)
*A61B 5/02* (2006.01)
*G16H 50/50* (2018.01)

(52) U.S. Cl.
CPC ........ *G06T 7/0012* (2013.01); *A61B 5/02028* (2013.01); *G06T 7/11* (2017.01); *G16H 50/50* (2018.01); *G06T 2207/10081* (2013.01); *G06T 2207/10108* (2013.01); *G06T 2207/30048* (2013.01)

(58) Field of Classification Search
None
See application file for complete search history.

(56) References Cited

U.S. PATENT DOCUMENTS

| 2020/0029926 A1 | 1/2020 | Sharma et al. |
| 2022/0093266 A1* | 3/2022 | Kosior .................. G16H 20/00 |

OTHER PUBLICATIONS

Raff et al., "Guidelines; SCCT guidelines for the interpretation and reporting of coronary computed tomographic angiography," 2009, Journal of Cardiovascular Computed Tomography, vol. 3, pp. 122-136.
Ortiz-Pérez et al., "Correspondence Between the 17-Segment Model and Coronary Arterial Anatomy Using Contrast-Enhanced Cardiac Magnetic Resonance Imaging," 2008, JACC: Cardiovascular Imaging, vol. 1, Issue 3, pp. 282-293.

* cited by examiner

Primary Examiner — Leon Flores

(57) ABSTRACT

Systems and methods for determining a concordance between results of medical assessments are provided. Results of a medical assessment of a first type for an anatomical object of a patient and results of a medical assessment of a second type for the anatomical object are received. The results of the medical assessment of the first type are converted to a hemodynamic measure. A concordance analysis between the results of the medical assessment of the first type and the results of the medical assessment of the second type based on the hemodynamic measure is performed. Results of the concordance analysis are output.

20 Claims, 16 Drawing Sheets

| # | Coronary Artery Segment | Severity |
|---|---|---|
| 1 | Proximal RCA | 0 |
| 2 | Mid RCA | 3 |
| 3 | Distal RCA | 0 |
| 4 | PDA-R | 0 |
| 5 | Left main | 0 |
| 6 | Proximal LAD | 3 |
| 7 | Mid LAD | 0 |
| 8 | Distal LAD | 0 |
| 9 | D1 | 0 |
| 10 | D2 | 0 |
| 11 | Proximal LCx | 0 |
| 12 | OM1 | 0 |
| 13 | Mid and distal LCx | 4 |
| 14 | OM2 | 0 |
| 15 | PDA-L | 0 |
| 16 | PLB-R | 0 |
| 17 | Ramus intermedius | 0 |
| 18 | PLB-L | 0 |

302 → #
304 → Coronary Artery Segment
306 → Severity
308 → (rows 1–18)

| | 502 | 504 | 506 |
|---|---|---|---|
| | # | LV Structures | Severity |
| | 1 | basal anterior | 1 |
| | 2 | basal anteroseptal | 0 |
| | 3 | basal inferoseptal | 0 |
| | 4 | basal inferior | 2 |
| | 5 | basal inferolateral | 2 |
| | 6 | basal anterolateral | 0 |
| | 7 | mid anterior | 0 |
| | 8 | mid anteroseptal | 2 |
| 508 | 9 | mid inferoseptal | 0 |
| | 10 | mid inferior | 0 |
| | 11 | mid inferolateral | 0 |
| | 12 | mid anterolateral | 0 |
| | 13 | apical anterior | 0 |
| | 14 | apical septal | 0 |
| | 15 | apical inferior | 0 |
| | 16 | apical lateral | 0 |
| | 17 | apex | 0 |

| Branch | Parent Branch |
|--------|---------------|
| 1 | N/A |
| 2 | 1 |
| 3 | 2 |
| 4 | 3 |
| 5 | N/A |
| 6 | 5 |
| 7 | 6 |
| 8 | 7 |
| 9 | 6 |
| 10 | 7 |
| 11 | 5 |
| 12 | 11 |
| 13 | 11 |
| 14 | 11 |
| 15 | 13 |
| 16 | 3 |
| 17 | 5 |
| 18 | 13 |

602 → Branch
604 → Parent Branch
606 } (rows 1–18)

| SPECT segment | LAD [%] | LCx [%] | RCA [%] |
|---|---|---|---|
| 1 | 100 | 0 | 0 |
| 2 | 100 | 0 | 0 |
| 3 | 0 | 0 | 100 |
| 4 | 0 | 0 | 100 |
| 5 | 0 | 100 | 0 |
| 6 | 0 | 100 | 0 |
| 7 | 100 | 0 | 0 |
| 8 | 100 | 0 | 0 |
| 9 | 0 | 0 | 100 |
| 10 | 0 | 0 | 100 |
| 11 | 0 | 100 | 0 |
| 12 | 0 | 100 | 0 |
| 13 | 100 | 0 | 0 |
| 14 | 100 | 0 | 0 |
| 15 | 0 | 0 | 100 |
| 16 | 0 | 100 | 0 |
| 17 | 100 | 0 | 0 |

| SPECT segment | LAD | LCx | RCA |
|---|---|---|---|
| 1 | 1 | 6 | -1 |
| 2 | 2 | -1 | 3 |
| 3 | 2 | -1 | 3 |
| 4 | -1 | 5 | 4 |
| 5 | -1 | 5 | 4 |
| 6 | 1 | 6 | -1 |
| 7 | 7 | 12 | -1 |
| 8 | 8 | -1 | 9 |
| 9 | 8 | -1 | -1 |
| 10 | -1 | 11 | 10 |
| 11 | -1 | 11 | 10 |
| 12 | 7 | 12 | -1 |
| 13 | 13 | 16 | -1 |
| 14 | 14 | -1 | 15 |
| 15 | 14 | 16 | 15 |
| 16 | 13 | 16 | 15 |
| 17 | 17 | -1 | -1 |

1210

CLINICAL DECISION SUPPORT FOR CARDIOVASCULAR DISEASE BASED ON A PLURALITY OF MEDICAL ASSESSMENTS

TECHNICAL FIELD

The present invention relates generally to clinical decision support for cardiovascular disease, and in particular to clinical decision support for cardiovascular disease based on a plurality of medical assessments.

BACKGROUND

Typically, multiple cardiovascular assessments are performed on patients during the course of their clinical care. However, there are no consistent and practical methods for comparing and contrasting results of the cardiovascular imaging assessments that take into consideration constraints that exist in routine clinical care. Such constraints may include, for example, unavailability of images and reports, incomplete reports, unstructured reports, non-typical cases (e.g., prior stents or bypasses), etc. In one conventional approach, image fusion is performed to fuse images of medical imaging assessments to compare and contrast the results of the medical imaging assessments. However, image fusion is not widely performed in the current clinical practice due to the constraints that exist in routine clinical care.

BRIEF SUMMARY OF THE INVENTION

In accordance with one or more embodiments, systems and methods for determining a concordance between results of medical assessments are provided. Results of a medical assessment of a first type for an anatomical object of a patient and results of a medical assessment of a second type for the anatomical object are received. The results of the medical assessment of the first type are converted to a hemodynamic measure. A concordance analysis between the results of the medical assessment of the first type and the results of the medical assessment of the second type based on the hemodynamic measure is performed. Results of the concordance analysis are output.

In one embodiment, the medical assessment of the first type is an anatomical assessment and the medical assessment of the second type is a functional assessment. The anatomical assessment may be based on CTA (computed tomography angiography) and the functional assessment may be based on SPECT (single-photon emission computerized tomography).

In one embodiment, the results of the medical assessment of the first type are converted to a hemodynamic measure by, for each respective segment of the anatomical object, determining a severity of the respective segment as a maximum of severities of the respective segment and parent segments of the respective segment.

In one embodiment, the concordance analysis is performed by determining a first concordance for each territory of the anatomical object by interrelating the hemodynamic measure to the medical assessment of the second type, determining a second concordance for each territory of the anatomical object by interrelating the results of the medical assessment of the second type to the medical assessment of the first type, and combining the first concordance and the second concordance to determine a final concordance for each territory of the anatomical object. A concordance for the patient may be determined based on the final concordance for each territory of the anatomical object.

In one embodiment, the concordance analysis is performed by defining a relationship matrix based on a coronary dominance of the patient and performing the concordance analysis based on the defined relationship matrix.

In one embodiment, the results of the medical assessment of the first type are generated to include results for one or more additional segments. A dictionary is updated to define a parent segment for each of the one or more additional segments and the results of the medical assessment of the first type are converted to the hemodynamic measure based on the updated dictionary. A relationship matrix is updated for the one or more additional segments. The concordance analysis between the generated results of the medical assessment of the first type and the results of the medical assessment of the second type is performed based on the updated relationship matrix and the updated dictionary.

In one embodiment, the results of the medical assessment of the first type are generated to include results for one or more bypass graft segments. A dictionary is updated to define a parent segment for each of the one or more bypass graft segments. The results of the medical assessment of the first type are converted to the hemodynamic measure based on the updated dictionary. The hemodynamic measure is updated by removing the one or more bypass graft segments from the hemodynamic measure. The concordance analysis between the generated results of the medical assessment of the first type and the results of the medical assessment of the second type is performed based on the updated hemodynamic measure.

In one embodiment, an anatomical model of the anatomical object is randomly varied. One or more stenoses are added to the randomly varied anatomical model. One or more flow rates are determined based on the randomly varied anatomical model with the one or more added stenoses. One or more functional defects are determined to each of a plurality of segments based on the one or more flow rates. A relationship matrix for performing the concordance analysis is adjusted based on the one or more stenoses and the one or more functional defects.

In one embodiment, the concordance analysis is performed based on a relationship matrix and the relationship matrix is updated based on 1) a first matrix representing a contribution of arteries of territories of the anatomical object to each segment of a functional model of the anatomical object and 2) a second matrix identifying, for each segment of the functional model, neighboring segments that are associated with a different territory within a ring level of the functional model.

These and other advantages of the invention will be apparent to those of ordinary skill in the art by reference to the following detailed description and the accompanying drawings.

BRIEF DESCRIPTION OF THE DRAWINGS

FIG. 3 shows exemplary results of a CTA (computed tomography angiography) anatomical assessment for stenoses in the coronary artery of a patient, in accordance with one or more embodiments;

FIG. 5 shows exemplary results of a SPECT (single-photon emission computerized tomography) functional assessment for a severity of perfusion deficit in the left ventricle of a patient, in accordance with one or more embodiments;

FIG. 6 shows a dictionary defining a parent segment for each segment in the 18-segment anatomical model, in accordance with one or more embodiments;

FIG. 12 shows an exemplary SPECT_SEGM_NEIGHB matrix, in accordance with one or more embodiments;

DETAILED DESCRIPTION

The present invention generally relates to clinical decision support for cardiovascular disease based on a plurality of medical assessments. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

The diagnosis of CAD (coronary artery disease) for a patient is typically based on both anatomical and functional assessments of the patient. While the functional assessment is generally considered to be more valuable than the anatomical assessment, to provide better support for clinical decision making, it is important to understand the concordance between the results of the anatomical assessment and the functional assessment. Advantageously, embodiments described herein provide for a concordance analysis between results of an anatomical assessment and results of a functional assessment for clinical decision support.

Figure 1:
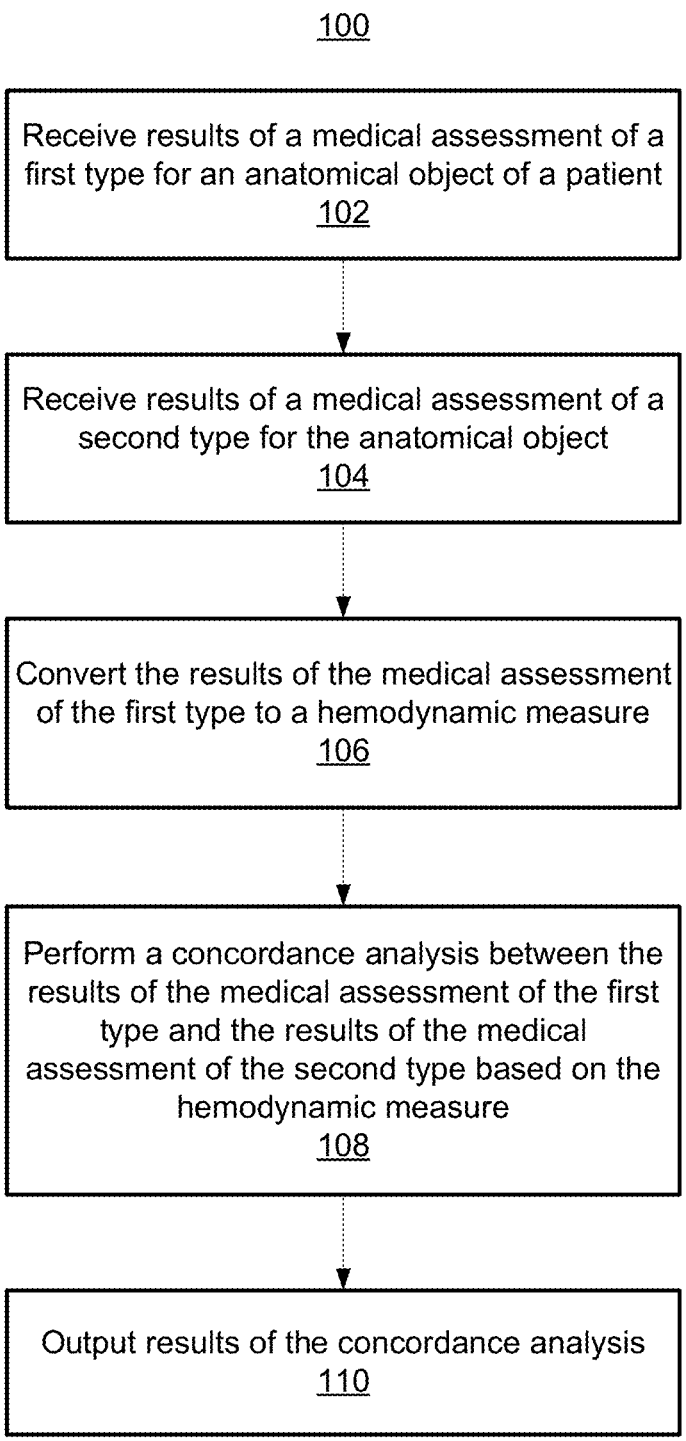
FIG. 1 shows a method for performing a concordance analysis between results of medical assessments, in accordance with one or more embodiments.

FIG. 1 shows a method 100 for performing a concordance analysis between results of medical assessments, in accordance with one or more embodiments. The steps of method 100 may be performed by one or more suitable computing devices, such as, e.g., computer 1002 of FIG. 10.

At step 102, results of a medical assessment of a first type for an anatomical object of a patient is received. In one embodiment, the anatomical object is the coronary artery of the patient for the evaluation of CAD (coronary artery disease). However, the anatomical object may be any suitable anatomical object of interest of the patient.

In one embodiment, the medical assessment of the first type is an anatomical assessment of the anatomical object. An anatomical assessment (also referred to as a morphological assessment or a structural assessment) is an assessment of the anatomy of the anatomical object. The anatomical assessment may be performed based on medical imaging, such as, e.g., CTA (computed tomography angiography) or any other suitable modality or modalities. The anatomical assessment may also be performed based on a physical assessment of the patient, such as, e.g., an invasive coronary angiography (ICA). It should be understood that the medical assessment of the second type may be any other suitable medical assessment and is not limited to an anatomical assessment.

Figure 2:
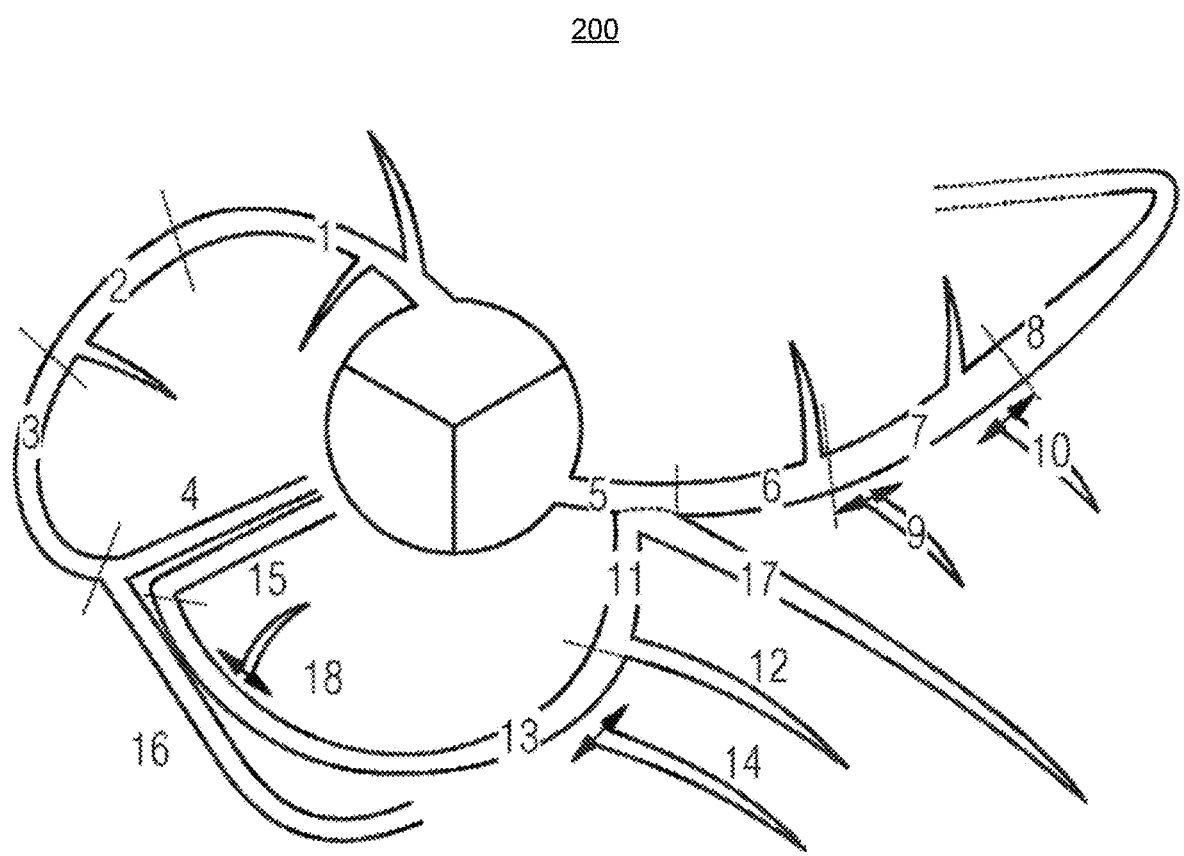
FIG. 2 shows an 18-segment anatomical model of coronary artery segmentation.

The medical assessments of the first type may be performed based on any suitable model of the anatomical object. For example, a CTA anatomical assessment may be based on an 18-segment anatomical model 200 of coronary artery segmentation according to the SCCT (Society of Cardiovascular Computed Tomography), as shown in FIG. 2. The results of the medical assessment of the first type may be represented in any suitable format, such as, e.g., a matrix or a table. The results of the medical assessment of the first type may be received by loading the results of the medical assessment of the first type from a storage or memory of a computer system or receiving the results of the medical assessment of the first type that have been transmitted from a remote computer system.

FIG. 3 shows exemplary results 300 of a CTA anatomical assessment for stenoses in the coronary artery of a patient, in accordance with one or more embodiments. In one example, results 300 are the results of the medical assessment of the first type in method 100 of FIG. 1 based on 18-segment anatomical model 200 of the coronary artery in FIG. 2. Results 300 are shown as a table having rows 308 corresponding to the 18 coronary artery segments of the 18-segment anatomical model of the coronary artery, column 302 identifying a number associated with the coronary artery segment according to the 18-segment anatomical model for the corresponding row 308, column 304 identifying the name of the coronary artery segment for the corresponding row 308, and column 306 identifying a severity of stenosis in the coronary artery segment for the corresponding row 308. In one embodiment, results 300 are generated by matrix multiplication of initial results of the CTA anatomical assessment and a CTA severity scale. Formulaically, results 300 of the CTA anatomical assessment may be calculated as follows:

UPDATED_FM_CTA=FM_CTA*CTA_SEVERITY_SCALE where UPDATED_FM_CTA denotes results 300 of the CTA anatomical assessment, FM_CTA denotes the initial results of the CTA anatomical assessment, CTA_SEVERITY_SCALE denotes the CTA severity scale, and * denotes the matrix multiplication operation. In one embodiment, results 400 of the CTA anatomical assessment may be generated as described in U.S. Patent Publication No. 2020/0029926, filed Dec. 13, 2018, the disclosure of which is incorporated by reference herein in its entirety.

At step 104 of FIG. 1, results of a medical assessment of a second type for the anatomical object are received.

In one embodiment, the medical assessment of the second type is a functional assessment of the anatomical object. A functional assessment (also referred to as a physiological imaging assessment) is an assessment of the physiological function of anatomical object. The functional assessment may be performed based on medical imaging, such as, e.g., SPECT (single-photon emission computerized tomography), PET (positron emission tomography), CMR (cardiac magnetic resonance) perfusion, CT (computed tomography) perfusion, ECG (echocardiography), or any other suitable modality or modalities. The functional assessment may also be performed based on a physical assessment of the patient, such as, e.g., wall motion assessment. It should be understood that the medical assessment of the second type may be any other suitable medical assessment and is not limited to a functional assessment.

Figure 4:
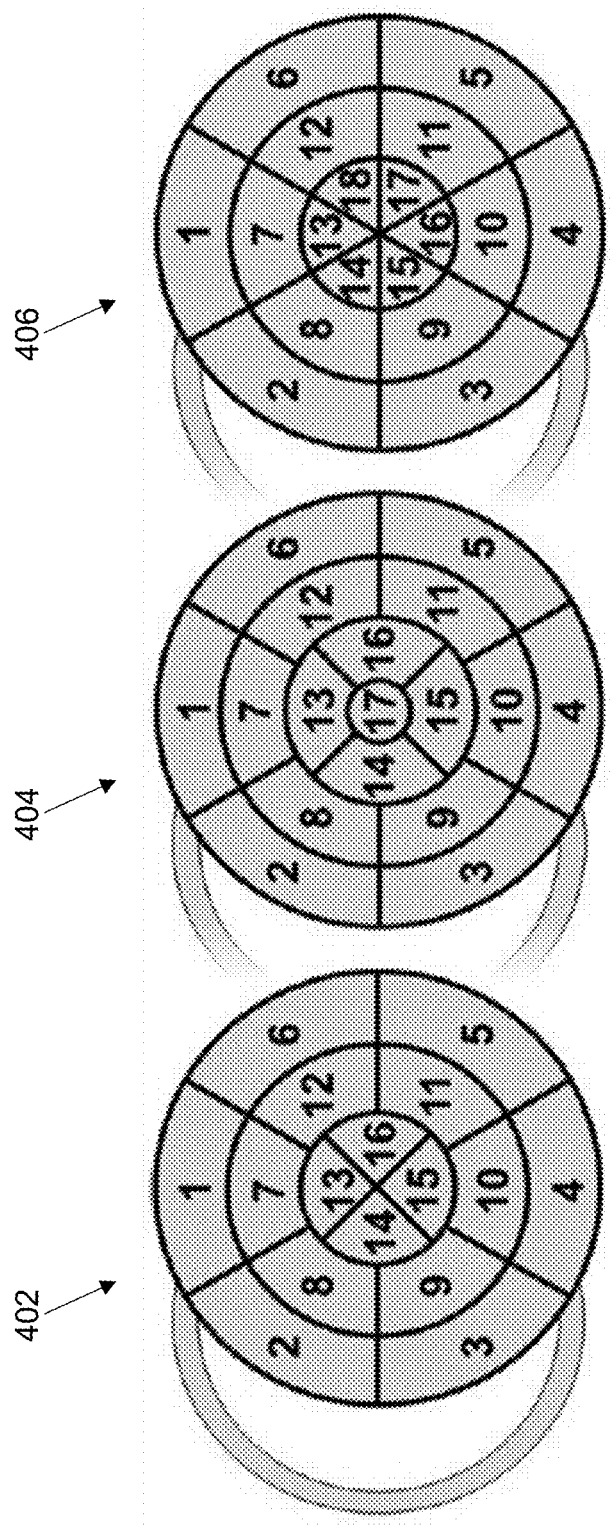
FIG. 4 shows functional models representing segmentation of the left ventricular myocardium, in accordance with one or more embodiments.

The medical assessments of the second type may be performed based on any suitable model of the anatomical object. For example, a SPECT functional assessment may be based on a 16-segment functional model 402, a 17-segment functional model 404, or an 18-segment functional model 406 represented as bullseye plots or polar plots representing segmentation of the left ventricular myocardium according to the AHA (American Heart Association), as shown in FIG. 4. The results of the medical assessment of the first type and the results of the medical assessment of the second type may be represented in any suitable format, such as, e.g., a matrix or a table. The results of the medical assessment of the second type may be received by loading the results of the medical assessment of the second type from a storage or memory of a computer system or receiving the results of the medical assessment of the second type that have been transmitted from a remote computer system.

FIG. 5 shows exemplary results 500 of a SPECT functional assessment for a severity of perfusion deficit in the LV (left ventricle) of a patient, in accordance with one or more embodiments. In one example, results 500 are the results of the medical assessment of the second type in method 100 of FIG. 1 based on 17-segment functional model 304 of the coronary artery in FIG. 3. Results 500 are shown as a table having rows 508 corresponding to 17 structures of the 17-segment functional model of the left ventricle, column 502 identifying a number associated with the structures of the left ventricle for the corresponding row 508, column 504 identifying the name of the structures of the left ventricle for the corresponding row 508, and column 506 identifying a severity of perfusion deficit in the structures of the left ventricle for the corresponding row 508. In one embodiment, results 500 are generated by matrix multiple of initial results of the SPECT functional assessment and a SPECT severity scale. Formulaically, results 500 of the SPECT functional assessment may be calculated as follows:

UPDATED_FM_SPECT=FM_SPECT*SPECT_SEVERITY_SCALE where UPDATED_FM_SPECT denotes results 400 of the SPECT functional assessment, FM_SPECT denotes the initial results of the SPECT functional assessment, SPECT_SEVERITY_SCALE denotes the SPECT severity scale, and * denotes the matrix multiplication operation. In one embodiment, results 500 of the SPECT functional assessment may be generated as described in U.S. Patent Publication No. 2020/0029926, filed Dec. 13, 2018, the disclosure of which is incorporated by reference herein in its entirety.

At step 106 of FIG. 1, the results of the medical assessment of the first type are converted to a hemodynamic measure. The hemodynamic measure may be any suitable measure of blood flow determined based only on the medical assessment of the first type (without using the results of the medical assessment of the second type), such as, e.g., FFR (fractional flow reserve), CFR (coronary flow reserve), pressure, flow, etc.

Formulaically, the results of the medical assessment of the first type is converted to a hemodynamic measure according to:

UPDATED_FM_CTA_FLOW=$f$(UPDATED_FM_CTA)

where UPDATED_FM_CTA_FLOW is the hemodynamic measure, UPDATED_FM_CTA is the results of the medical assessment of the first type, and f is a function for converting the results of the medical assessment of the first type to the hemodynamic measure.

The results of the medical assessment of the first type may be converted to the hemodynamic measure using any suitable function $f$. In one embodiment, the function $f$ for converting the results of the medical assessment of the first type to the hemodynamic measure is an algorithm. For example, the algorithm may be a CFD (computational fluid dynamics) based algorithm or a machine learning based model. In one embodiment, where medical images of the anatomical structures of interest are available, a patient-specific anatomical model of the anatomical object (e.g., the coronary artery) may be constructed based on the medical images and used as input into the algorithm. In another embodiment, for example where the medical images of the anatomical object are not available, a population-averaged healthy anatomical model of the anatomical object may be employed and adapted to the patient-specific pathological state by, e.g., introducing stenoses with a severity and at a location as specified in the results of the medical assessment of the first type. The adapted anatomical model may be used as input into the CFD based algorithm for computing flows and pressures.

In one embodiment, the function $f$ for converting the results of the medical assessment of the first type to the hemodynamic measure is based on a dictionary CTA_SEGM_PARENT defining the parent for each segment in the anatomical model of the anatomical object. Dictionary CTA_SEGM_PARENT is utilized to convert the anatomical severity of a stenosis in each segment to a functional severity. The dictionary may be represented as a table or any other suitable format. FIG. 6 shows a dictionary 600 defining a parent segment for each segment (or branch) in the 18-segment anatomical model, in accordance with one or more embodiments. Dictionary 600 is shown as a table having rows 606 corresponding to the 18 coronary artery segments of the 18-segment anatomical model, column 602 identifying a number associated with the coronary artery segment according to the 18-segment anatomical model for the corresponding row 606, and column 604 identifying the parent segment for the corresponding row 606. Using dictionary 600, the function $f$ may be implemented as:

UPDATED_FM_CTA_FLOW[$i$]=max(UPDATED_FM_CTA[$i$],upstream_segments(UPDATED_FM_CTA[$i$]))

where the index i denotes a coronary artery segment in the anatomical model and upstream_segments(UPDATED_FM_CTA[i]) denotes function $f$ that returns the parent segment of the segment UPDATED_FM_CTA[i]. The functional severity of each respective segment i is determined as the maximum of the anatomical severities of the respective segment i and all parent segments of the respective segment i. This is because if a stenosis is present in a segment, it will functionally affect all downstream segments.

In some embodiments, the hemodynamic measure may be normalized as:

UPDATED_FM_CTA_FLOW=UPDATED_FM_CTA_FLOW/ max(CTA_SEVERITY_SCALE)

At step 108 of FIG. 1, a concordance analysis between the results of the medical assessment of the first type and the results of the medical assessment of the second type is performed based on the hemodynamic measure. The concordance analysis determines a level of concordance or agreement between the results of the medical assessment of the first type and the results of the medical assessment of the second type.

The concordance analysis is performed to determine a level of concordance for each of one or more territories of the anatomical object. For example, where the anatomical object is the coronary artery, the territories of the coronary artery may include the LAD (left anterior descending) artery, LCx (left circumflex) artery, and RCA (right coronary artery). Each territory comprises one or more segments or branches of the coronary artery (e.g., segments of 18-segment anatomical model 200 of coronary artery segmentation or segments of 16-segment functional model 402, 17-segment functional model 404, or 18-segment functional model 406 representing segmentation of the left ventricular myocardium).

In one embodiment, the concordance analysis is performed by 1) determining a first concordance by interrelating the hemodynamic measure to the medical assessment of the second type and 2) determining a second concordance by interrelating the results of the medical assessment of the second type to the medical assessment of the first type. The first concordance and the second concordance are then combined to determine a final concordance.

To calculate the first concordance, relationship matrix $RM\_{CTA \rightarrow SPECT}$ is defined to interrelate the hemodynamic measure to the medical assessment of the second type. The relationship matrix $RM\_{CTA \rightarrow SPECT}$ comprises indicators of interrelatedness (or weights of association) between coronary artery segments (e.g., according to the 18-segment anatomical model) and myocardial perfusion segments (e.g., according to the 17-segment functional model). In one embodiment, the relationship matrix $RM\_{CTA \rightarrow SPECT}$ is a general relationship matrix for a global population. In another embodiment, the relationship matrix $RM\_{CTA \rightarrow SPECT}$ is a patient-specific relationship matrix defined, e.g., based on medical images and other patient information of the patient. In one embodiment, the relationship matrix $RM\_{CTA \rightarrow SPECT}$ is normalized as follows:

$$NORM\_RM\_{CTA \rightarrow SPECT}(i,j) = RM\_{CTA \rightarrow SPECT}(i,j) / \Sigma_i RM\_{CTA \rightarrow SPECT}(i,j)$$

wherein $NORM\_RM\_{CTA \rightarrow SPECT}$ denotes the normalized relationship matrix interrelating CTA to SPECT, $RM\_{CTA \rightarrow SPECT}$ denotes the relationship matrix interrelating CTA to SPECT, index i denotes a segment in the CTA anatomical assessment, and index j denotes a segment in the SPECT functional assessment.

A difference vector $\Delta V\_SPECT$ is then calculated to compare the interrelated hemodynamic measure to the results of the medical assessment of the second type. In particular, difference vector $\Delta V\_SPECT$ is calculated between 1) the matrix product of the hemodynamic measure and the normalized relationship matrix $NORM\_RM\_{CTA \rightarrow SPECT}$ and 2) the results of the medical assessment of the second type. Each entry in difference vector $\Delta V\_SPECT$ represents a concordance value for a segment in the functional model. Formulaically, the difference vector $\Delta V\_SPECT$ is calculated as follows:

$$\Delta V\_SPECT = abs((UPDATED\_FM\_CTA\_FLOW * NORM\_RM\_{CTA \rightarrow SPECT}) - UPDATED\_FM\_SPECT)$$

The first concordance is then calculated for each territory of the anatomical object (e.g., the coronary artery). For example, the territories of the coronary artery may comprise the LAD, LCx, and RCA. A vector for each territory is defined to identify the segments (e.g., of functional models 402, 404, or 406 in FIG. 4 representing segmentation of the left ventricular myocardium) in the territories. In one example, the following vectors are defined for the LAD, LCx, and RCA territories:

$$SPECT\_LAD = [1,1,0,0,0,0,1,1,0,0,0,0,1,1,0,0,1]^T$$

$$SPECT\_LCx = [0,0,0,0,1,1,0,0,0,0,1,1,0,0,0,1,0]^T$$

$$SPECT\_RCA = [0,0,1,1,0,0,0,0,1,1,0,0,0,0,1,0,0]^T$$

where each position within the vector is associated with a segment and a 1 indicates that the segment corresponding to that position in the vector is located within the territory while a 0 indicates that a segment corresponding to that position in the vector is not located within the territory. The first concordance is then computed for each territory as:

$$\Delta V\_SPECT\_CONCORDANCE = \text{compute\_concordance}(\Delta V\_SPECT, SPECT\_LAD, SPECT\_LCx, SPECT\_RCA)$$

where compute_concordance is a function which determines a concordance value for each respective territory (e.g., LAD, LCx, RCA) as a maximum of the absolute concordance values of segments in the difference vector $\Delta V\_SPECT$ for the segments in the respective territory as defined in vectors SPECT_LAD, SPECT_LCx, and SPECT_RCA.

To calculate the second concordance, a relationship matrix $RM\_{SPECT \rightarrow CTA}$ is defined to interrelate the results of the medical assessment of the second type to the medical assessment of the first type. In one embodiment, relationship matrix $RM\_{SPECT \rightarrow CTA}$ is the same as relationship matrix $RM\_{CTA \rightarrow SPECT}$ but transposed. However, in other embodiments, relationship matrix $RM\_{SPECT \rightarrow CTA}$ and relationship matrix $RM\_{CTA \rightarrow SPECT}$ are different matrices. In one embodiment, the relationship matrix $RM\_{SPECT \rightarrow CTA}$ may be normalized as follows:

$$NORM\_RM\_{SPECT \rightarrow CTA}(i,j) = RM\_{SPECT \rightarrow CTA}(i,j) / \Sigma_i RM\_{SPECT \rightarrow CTA}(i,j)$$

wherein $NORM\_RM\_{SPECT \rightarrow CTA}$ denotes the normalized relationship matrix interrelating SPECT to CTA, $RM\_{SPECT \rightarrow CTA}$ denotes the relationship matrix interrelating SPECT to CTA, index i denotes a segment in the SPECT functional assessment, and index j denotes a segment in the CTA anatomical assessment.

A difference vector $\Delta V\_CTA$ is then calculated to compare the interrelated results of the medical assessment of the second type to the results of the medical assessment of the first type. In particular, difference vector $\Delta V\_CTA$ is calculated between 1) the matrix product of the results of the medical assessment of the second type and the normalized relationship matrix NORM_RM$_{SPECT \to CTA}$ and 2) the hemodynamic measure. Each entry in difference vector ΔV_CTA represents a concordance value for a segment in the functional model. Formulaically, the difference vector ΔV_CTA is calculated as follows:

$$\Delta V\_CTA = abs((UPDATED\_FM\_SPECT * NORM\_RM_{SPECT \to CTA}) - UPDATED\_FM\_CTA\_FLOW)$$

The second concordance is then calculated for each territory of the anatomical object (e.g., the coronary artery). A vector for each territory is defined to identify the segments (e.g., of anatomical model 200 of coronary artery segmentation) in the territories. In one example, the following vectors are defined for the LAD, LCx, and RCA territories:

$$CTA\_LAD=[0,0,0,0,1,1,1,1,1,0,0,0,0,0,0,1,0]^T$$

$$CTA\_LCx=[0,0,0,0,1,0,0,0,0,0,1,1,1,1,1,0,1,1]^T$$

$$CTA\_RCA=[1,1,1,1,0,0,0,0,0,0,0,0,0,0,0,1,0,0]^T$$

where each position within the vector is associated with a segment and a 1 indicates that the segment corresponding to that position in the vector is located within the territory while a 0 indicates that a segment corresponding to that position in the vector is not located within the territory.

The second concordance is then computed for each territory as:

$$\Delta V\_CTA\_CONCORDANCE=compute\_concordance (\Delta V\_CTA, CTA\_LAD, CTA\_LCx, CTA\_RCA)$$

where compute_concordance is a function which determines a concordance value for each respective territory (e.g., LAD, LCx, RCA) by taking the maximum of the absolute concordance values in the difference vector ΔV_SPECT for the segments in that respective territory as defined in vectors SPECT_LAD, SPECT_LCx, and SPECT_RCA.

The first concordance and the second concordance are then combined to determine a final concordance between the results of the medical assessment of the first type and the results of the medical assessment of the second type. For example, the first concordance and the second concordance may be combined by averaging the concordance vectors ΔV_SPECT_CONCORDANCE and ΔV_CTA_CONCORDANCE for each territory as follows:

$$\Delta V\_CONCORDANCE=mean(\Delta V\_SPECT\_CONCORDANCE, \Delta V\_CTA\_CONCORDANCE)$$

where ΔV_CONCORDANCE has a concordance value between 0 and 1, where 0 corresponds to perfect concordance and 1 corresponds to complete discordance. Other approaches for combining the concordance analyses may also be employed (e.g., by computing the median of the concordance analyses).

In one embodiment, the concordance value ΔV_CONCORDANCE may be compared to one or more thresholds to classify the concordance at each territory. For example, a concordance value between 0 and 0.25 may be classified as having concordance, a concordance value between 0.25 and 0.5 may be classified as having mild concordance, a concordance value between 0.5 and 0.75 may be classified as having moderate concordance, and a concordance value between 0.75 and 1.0 may be classified as having severe discordance.

In one embodiment, a patient-level concordance may be calculated as the maximum concordance value of each of the territories as follows:

$$CONCORDANCE\_PATIENT=max(\Delta V\_CONCORDANCE)$$

At step 110, results of the concordance analysis are output. For example, the results of the concordance analysis can be output by displaying the results of the concordance analysis on a display device of a computer system, storing the results of the concordance analysis on a memory or storage of a computer system, or by transmitting the results of the concordance analysis to a remote computer system. The results of the concordance analysis may be utilized for clinical decision support. For example, the results of the concordance analysis may be output to a clinical decision support system for automatically determining a suggested course of action (e.g., recommended treatments or tests).

In one embodiment, the relationship matrices utilized in the concordance analysis at step 108 of FIG. 1 may be patient specific relationship matrices defined based on the coronary dominance of the patient. Coronary dominance is defined based on the arteries that supply the PDA (posterior descending artery) and the PLB (posterior-lateral branch). Right dominance is where the PDA and PLB are supplied by the RCA (right coronary artery), left dominance is where the PDA and PLB are supplied by the LCx, and co-dominance is where the PDA and PLB are supplied by both the RCE and the LCx.

Figure 7:
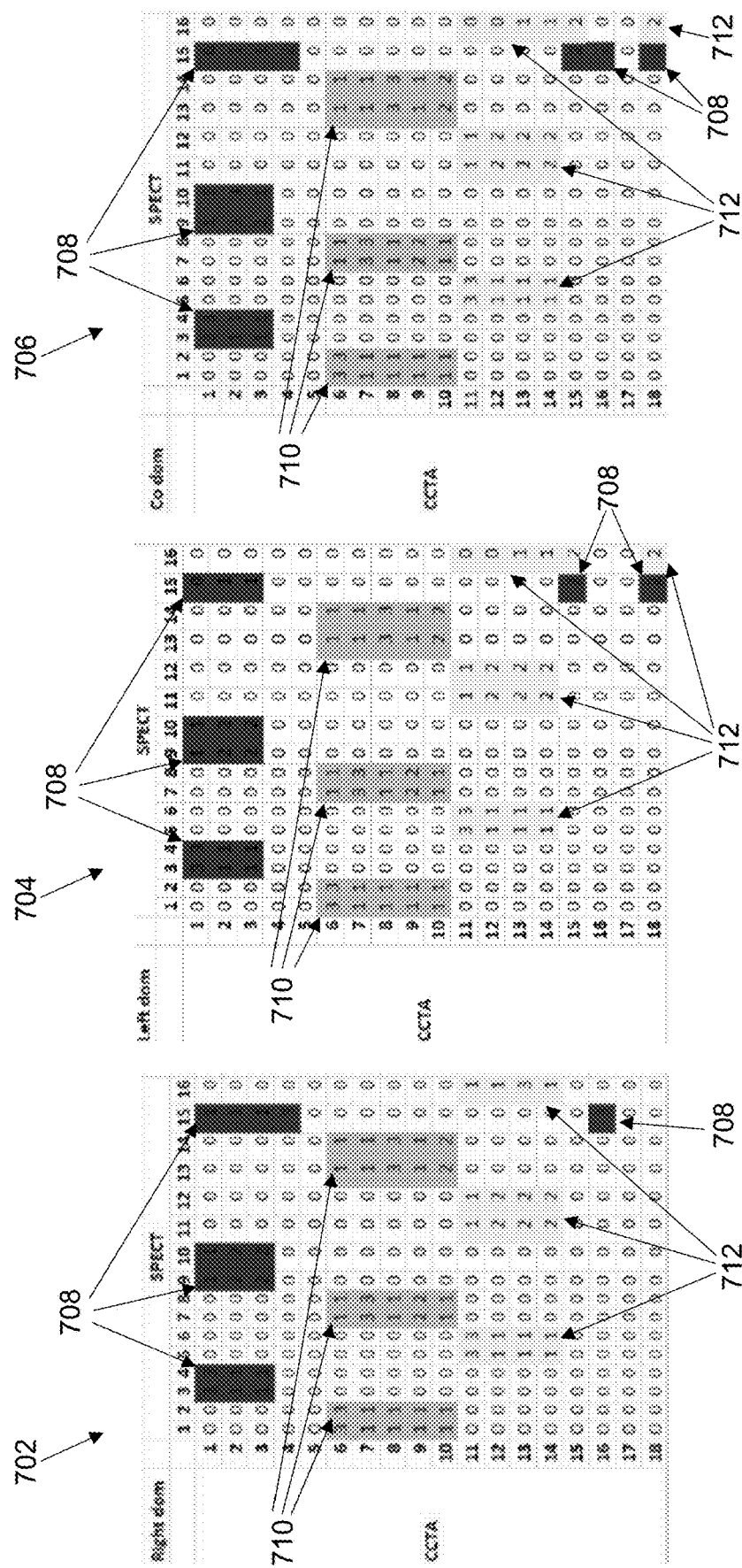
FIG. 7 shows relationship matrices for a 16-segment functional model of myocardial perfusion segments adapted for a coronary dominance of the patient, in accordance with one or more embodiments.
Figure 8:
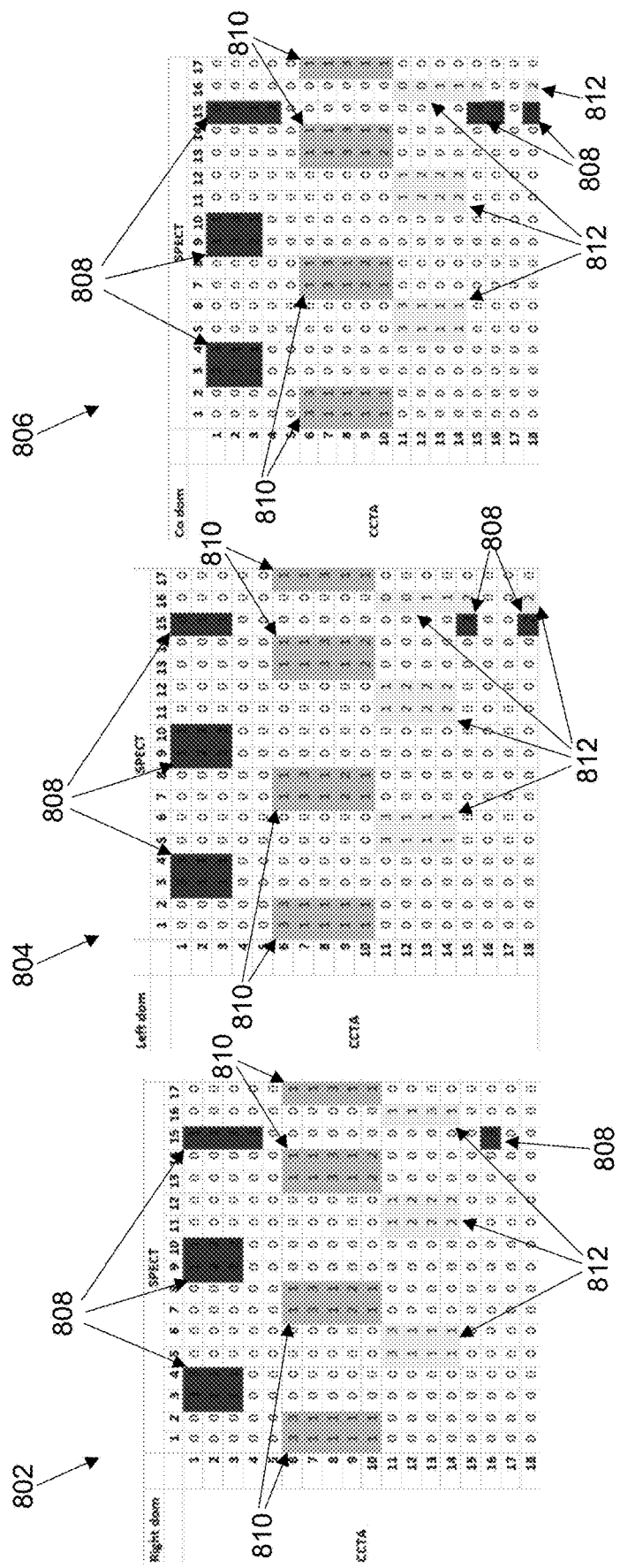
FIG. 8 shows relationship matrices for a 17-segment functional model of myocardial perfusion segments adapted for a coronary dominance of the patient, in accordance with one or more embodiments.
Figure 9:
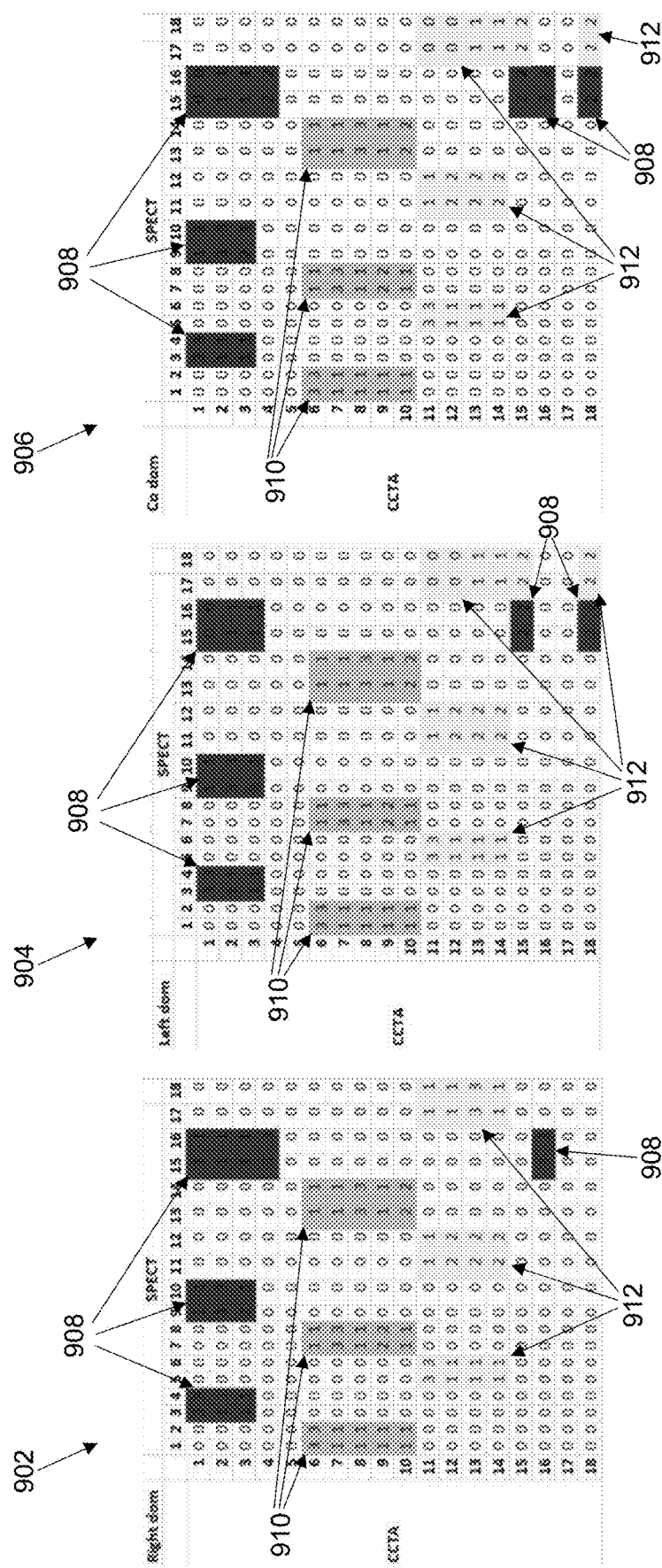
FIG. 9 shows relationship matrices for an 18-segment functional model of myocardial perfusion segments adapted for a coronary dominance of the patient, in accordance with one or more embodiments.

To adapt the concordance analysis for right, left, or co-dominance of the patient, the relationship matrices are defined based on the coronary dominance of the patient. For example, for the 16-segment functional model of myocardial perfusion segments, the relation matrix RM$_{CTA \to SPECT}$ may be relationship matrix 702, 704, or 706 in FIG. 7 for a right dominant patient, a left dominant patient, and a co-dominant patient, respectively, in accordance with one or more embodiments, where cells 708 correspond to the RCA, cells 710 correspond to the LAD, and cells 712 correspond to the LCx. In another example, for the 17-segment functional model of myocardial perfusion segments, the relation matrix RM$_{CTA \to SPECT}$ may be relationship matrix 802, 804, or 806 in FIG. 8 for a right dominant patient, a left dominant patient, and a co-dominant, respectively, in accordance with one or more embodiments, where cells 808 correspond to the RCA, cells 810 correspond to the LAD, and cells 812 correspond to the LCx. In another example, for the 18-segment functional model of myocardial perfusion segments, the relationship matrix RM$_{CTA \to SPECT}$ may be relationship matrix 902, 904, or 906 in FIG. 9 for a right dominant patient, a left dominant patient, and a co-dominant patient, respectively, in accordance with one or more embodiments, where cells 908 correspond to the RCA, cells 910 correspond to the LAD, and cells 912 correspond to the LCx. The relationship matrices in FIGS. 7-9 are adapted based on the number of SPECT segments and the dominance of the patient. For the number of SPECT segments, different arteries supply different segments. The differences are encountered only for segments 13 to 16/17/18 (depending on the model). For the dominance of the patient, the coronary artery has minor variations that may or may not be present in segments 4, 15, 16, and/or 18, which are reflected in the relationship matrices.

The segments in each territory are then updated based on the coronary dominance of the patient. For example, in the 16-segment functional model, vectors SPECT_LAD, SPECT_LCx, and SPECT_RCA are defined to identify segment 14 as being supplied only by the RCA in right dominant patients and by both the RCA and LCx in left dominant and co-dominant patients. In the 17-segment functional model, vectors SPECT_LAD, SPECT_LCx, and SPECT_RCA are defined to identify segment 14 as being supplied only by the RCA in right dominant patients and by both the RCA and LCx in left dominant and co-dominant patients. In the 18-segment functional model, vectors SPECT_LAD, SPECT_LCx, and SPECT_RCA are defined to identify segments 14 and 15 as being supplied only by the RCA in right dominant patients and by both the RCA and LCx in left dominant and co-dominant patients.

The patient-specific relationship matrix may be derived from medical images of the patient depicting the anatomical object (e.g., the coronary arteries). In particular, a coronary anatomical model is constructed from the medical images and mapped to the myocardium. The myocardium is divided into segments (e.g., according to the 16, 17, or 18 segment functional models) and, for each respective segment of the myocardium, a segment supplying the respective segment is identified by determining a closest coronary segment from the respective segment. Subtending arteries are then determined for each of the segments. For example, segment 17 may be subtended 90% by the LAD and 10% by the RCA. Values of the relationship matrix are then defined based on the subtending arteries. Accordingly, if a myocardial (SPECT) segment is supplied by a certain coronary artery (i.e., the closest coronary branch), the corresponding value in the relationship matrix is non-zero and otherwise it is zero. Depending on the number and importance (e.g., size) of arteries supplying a myocardial segment the non-zero value may be greater or smaller.

In one embodiment, method 100 of FIG. 1 may be modified to introduce one or more additional segments to the anatomical model (e.g., the 18-segment anatomical model) of the coronary artery utilized in the anatomical assessment. Typically, a patient may have many additional segments that are discarded under the 18-segment model due to their relatively small size and unimportance. However, some patients may have significantly large coronary segments that are not represented in the standard 18-segment model. To account for such segments in the concordance analysis, in addition to the initial results FM_CTA of the anatomical assessment, initial additional results FM_CTA_OTHER is defined. Similar to FM_CTA, FM_CTA_OTHER comprises a row for each additional segment and a plurality of columns corresponding to different severities of a stenosis, where the values on each row represent a one hot encoded value for the severity of a stenosis such that a row for an additional segment has a value of 1 in the column corresponding to the severity and a 0 in the remaining columns corresponding to the severities.

Additionally, FM_CTA_OTHER_BRANCH and FM_CTA_OTHER_LOCATION are defined. FM_CTA_OTHER_BRANCH identifies the territory where the additional segments are positioned (e.g., LAD, LCx, or RCA). FM_CTA_OTHER_BRANCH comprises a row for each additional segment and a plurality of columns corresponding to the different territories, where a row for an additional segment has a value of 1 in the column corresponding to the territory of the additional segment and a 0 in the remaining columns corresponding to the other territories. FM_CTA_OTHER_LOCATION identifies the anatomical location (e.g., proximal, mid, or distal) of the additional segment with respect to the territory. FM_CTA_OTHER_LOCATION comprises a row for each additional segment and a plurality of columns corresponding to the different anatomical locations, where the values on each row represent a one hot encoded value for the anatomical location of a segment such that a row for an additional segment has a value of 1 in the column corresponding to the anatomical location of the additional segment and a 0 in the remaining columns corresponding to the other anatomical locations.

Method 100 of FIG. 1 is modified to incorporate the additional segments by first generating the results of the medical assessment of the first type to include results for the additional segments by appending FM_CTA with the contents of FM_CTA_OTHER. Relationship matrix $RM_{CTA \rightarrow SPECT}$ is updated for the additional segments by adding one additional row for each additional segment in FM_CTA_OTHER. In particular, segments in the functional model that correspond to the additional segments are determined based on the territory and location of the additional segments. For example, if an additional segment is in the proximal LAD, the corresponding segments in the functional model are determined as segments 1 and 2. Next, an additional row is added to relationship matrix $RM_{CTA \rightarrow SPECT}$ comprising a value of 3 in the columns corresponding to the determined segments (e.g., segments 1 and 2 in the example) and a value of 0 in the remaining columns. Dictionary CTA_SEGM_PARENT is then updated to add a row for each additional segment in FM_CTA_OTHER, where each additional segment is numbered in ascending order (e.g., 19, 20, etc.) and its parent segment is defined based on the territory and location in FM_CTA_OTHER_BRANCH and FRM_CTA_OTHER_LOCATION respectively. Method 100 then proceeds to perform the concordance analysis based on the updated relationship matrix and the updated dictionary.

In one embodiment, method 100 of FIG. 1 may be modified to account for coronary artery bypass grafts. CABG (coronary-artery bypass grafting) is a procedure in which autologous arteries or veins are used as grafts to bypass coronary arteries that are partially or completely obstructed by atherosclerotic plaque. To account for bypass graft segments in the concordance analysis, in addition to the initial results FM_CTA of the anatomical assessment, initial additional results FM_CTA_CAGB is defined for the graft segments. Similar to FM_CTA, FM_CTA_CABG comprises a row for each graft segment and a plurality of columns corresponding to different severities of a stenosis in the graft segments, where values on each row represent a one hot encoded value for the severity of a stenosis such that a row for a graft segment has a value of 1 in the column corresponding to the severity and a 0 in the remaining columns corresponding to the severities.

Additionally, FM_CTA_CABG_BRANCH and FM_CTA_CABG_LOCATION are defined. FM_CTA_CABG_BRANCH identifies the territory that the graft segments are positioned (e.g., LAD, LCx, or RCA). FM_CTA_CABG_BRANCH comprises a row for each graft segment and a plurality of columns corresponding to the different territories, where values on each row represent a one hot encoded value for the territory of the graft segment such that a row for a graft segment has a value of 1 in the column corresponding to the territory of the graft segment and a 0 in the remaining columns corresponding to the other territories. FM_CTA_CABG_LOCATION identifies the anatomical location (e.g., proximal, mid, or distal) of the graft segment with respect to the territory. FM_CTA_CABG_LOCATION comprises a row for each graft segment and a plurality of columns corresponding to the different anatomical locations, where values on each row represent a one hot encoded value for the anatomical location of the graft segment such that a row for a graft segment has a value of 1 in the column corresponding to the anatomical location of the graft segment and a 0 in the remaining columns corresponding to the other anatomical locations.

Method 100 of FIG. 1 is modified to incorporate the graft segments by generating the results for the medical assessment of the first type to include results for the bypass graft segments by appending FM_CTA with the contents of FM_CTA_CABG. Dictionary CTA_SEGM_PARENT is then updated to define a parent segment for each of the bypass graft segments by adding a row for each graft segment in FM_CTA_CABG, where each graft segment is numbered in ascending order (e.g., 19, 20, etc.) and its parent segment is defined based on the territory and location in FM_CTA_CAGB_BRANCH and FM_CTA_CABG_LOCATION respectively. UPDATED_FM_CTA and UPDATED_FM_CTA_FLOW are then computed based on the appended FM_CTA. Subsequently, UPDATED_FM_CTA_FLOW is updated to remove the grafts segments from UPDATED_FM_CTA_FLOW and method 100 proceeds to perform the concordance analysis based on the updated hemodynamic measure. The graft segments are removed from the concordance analysis since they are not directly supplying any myocardium. The myocardium is supplied only by native coronary arteries, which in turn may be supplied by the graft segments. Given the approach for computing UPDATED_FM_CTA_FLOW, the effect of a stenosis on the graft segment is expressed in UPDATED_FM_CTA_FLOW. The effect of a stenosis is expressed in the perfusion results and, hence, method 100 provides for the concordance even in the presence of graft segments.

In one embodiment, method 100 of FIG. 1 may be evaluated and fine-tuned using synthetic data. While method 100 may be evaluated and fine-tuned using patient-specific data, synthetic data has the advantage that rare or complex cases can be set up for a more thorough evaluation and fine-tuning.

In one embodiment, the synthetic data may be generated based on a population averaged 3D anatomical model of the anatomical object (e.g., the coronary artery). Random variations are added to the coronary artery model by, for example, changing the centerline course, adding or removing side branches, modifying coronary dominance, modifying healthy radiuses, etc. Next, one or more stenoses are added to the coronary anatomical model and flow rates at rest and hyperemia are determined based on the coronary anatomical model by, e.g., running CFD (computational fluid dynamics) simulations or using an AI-based model. The coronary anatomical model is then mapped to the myocardium and the myocardium is divided into segments (e.g., 16, 17, or 18 segments). Territories are determined for each vessel, for example, by determining a closest coronary segment for each segment of the myocardium. The closest coronary segment is considered to supply that segment of the myocardium. A functional defect is determined for each segment of the myocardium based on the rest and hyperemia flow rates. Accordingly, synthetic data with perfect concordance between anatomical results (e.g., the stenoses) and functional results (e.g., the functional defects) is generated. Different levels of discordance may be added by introducing random variations in the functional defects. The concordance analysis may then be fine-tuned based on the synthetic data by, e.g., adjusting values of the relation matrix.

In another embodiment, the synthetic data may be generated by modifying method 100 to generate SPECT data from CTA data or CTA data from SPECT data. In particular, UPDATED_FM_CTA_TO_SPECT is calculated as follows:

UPDATED_FM_CTA_TO_SPECT=UPDATED_FM_CTA_FLOW*NORM_RM$_{CTA \to SPECT}$ and UPDATED_SYNTHETIC_SPECT is calculated as:

UPDATED_SYNTHETIC_SPECT=UPDATED_FM_CTA_TO_SPECT*SPECT_SEVERITIES_NORM and SYNTHETIC_SPECT is calculated as:

SYNTHETIC_SPECT=$g$(UPDATED_SYNTHETIC_SPECT)

where $g$ is a function that converts UPDATED_SYNTHETIC_SPECT into a one-hot encoded format, UPDATED_FM_CTA_TO_SPECT represents the CTA data converted to SPECT, UPDATED_SYNTHETIC_SPECT represents the updated converted SPECT data, and SYNTHETIC_SPECT represents synthetic SPECT data. Accordingly, the CTA data is converted to SPECT data (UPDATED_FM_CTA_TO_SPECT), which are then converted back to the original SPECT data format (SYNTHETIC_SPECT).

In one embodiment, the concordance analysis performed at step 106 of FIG. 1 is performed using one or more machine learning based models. The machine learning based models may be trained based on real patient data or synthetic data generated in accordance with embodiments described herein.

In one example, a machine learning based model may be applied to determine the relationship matrix by, e.g., choosing a most appropriate relationship matrix from an existing set of relationship matrices (multi-class classification problem) or determining the values of the relationship matrix (regression problem). In both cases, input data comprising patient-specific information (e.g., medical reports, medical images, etc.) is input into a machine learning based model and a relationship matrix or values of a relationship matrix is output.

In another example, a machine learning based model may be applied to directly determine a concordance between the medical assessments of the first type and the second type, e.g., at a segment level, at a territory level, and/or at a patient level. A machine learning based model trained with multi-task learning may be employed to simultaneously output the concordance at the segment level, the territory level, and the patient level. Data programming may be employed within the learning task. Noisy training labels may be exploited by specifically encoding a weak supervision in the form of labeling functions. Labeling functions may have widely varying error rates and may conflict on certain data points. They can be modeled as a generative process, leading to an automated denoising by learning the accuracies of the labeling functions along with their correlation structure. A labeling function represents a pattern that a user wishes to impart to their model, which is easier to encode as a labeling function as compared to a set of hand-labeled examples. Labeling functions can be based on external knowledge bases, libraries, or ontologies, can express heuristic patterns, or some hybrid of these types. The use of labeling functions is also more general than manual annotations, as a manual annotation can always be directly encoded by a labeling function. Labeling functions can overlap, conflict, and event have dependencies which users can provide as part of the data programming specification. In some embodiments, the labeling function can assign an "abstain" value.

In another example, a cascaded of machine learning based models may be applied for determining a concordance between medical assessments of the first type and the second type. A first machine learning based model may be trained to predict an initial concordance. The first machine learning based model may be trained on synthetically generated data using, e.g., ground truth concordance values computed according to method 100 of FIG. 1. A second machine learning based model may be trained to predict a final concordance. The second machine learning based model receives as input the output of the first machine learning based model and patient-specific information (not used to compute the ground truth values for training the first machine learning based model). Exemplary patient-specific information may include the presence of previous stents (for which in-stent restenosis cannot be evaluated on CTA data), microvascular disease (which limits the hyperemic response even in the absence of significant stenoses), etc.

In one embodiment, the medical assessment of the first type and the medical assessment of the second type in method 100 of FIG. 1 are both anatomical assessments. For example, the anatomical assessment of the first type and the anatomical assessment of the second type may be based on different imaging modalities or the anatomical assessment of the first type may be based on imaging (e.g., CTA) and the anatomical assessment of the second type may be based on patient measurements (e.g., ICA (invasive coronary angiography)). In this embodiment, the relationship matrix is not used and a concordance analysis can be performed directly from the results of the anatomical assessments. While CTA allows for the visualization and assessment of all coronary arteries, ICA may not have findings for all coronary segments (e.g., due to missing views, vessel overlap, or foreshortening). In this case, assumptions may be made for the coronary segments without findings (e.g., healthy/mild disease, depending on the results of the other segments).

In one embodiment, the medical assessment of the first type and the medical imaging assessment of the second type in method 100 of FIG. 1 are both functional imaging assessments. For example, the functional assessment of the first type and the functional assessment of the second type may be based on different imaging modalities or the functional assessment of the first type may be based on imaging (e.g., CMR perfusion) and the functional assessment of the second type may be based on patient measurements (e.g., wall motion assessment from stress echo). In this embodiment, the interrelating using the relationship matrix may or may not be performed. For example, the interrelating may be performed if the format is different (e.g., results of the medical assessment of the first type uses a 16-segment model and results of the medical assessment of the second type uses an 18-segment model). Assumptions may also be made for segments without findings based on findings of neighboring segments (e.g., a moderate defect may be assumed next to a segment found to have a severe defect).

In one embodiment, method 100 of FIG. 1 may be incorporated in a clinical decision support system. For instance, an algorithm may suggest a decision based on the output of the concordance analysis of method 100. In one example, where results of the concordance analysis indicate concordance (e.g., complete concordance or mild discordance), the clinical decision support system may provide a suggested course of action to finalize a diagnosis and plan treatment (e.g., an optimal medical treatment such as CABG or PCI (percutaneous coronary intervention)). In another example, where results of the concordance analysis indicate discordance (e.g., moderate or severe discordance), the clinical decision support system may provide a suggested course of action to order a new test to clarify the discordance. In one embodiment, the suggested course of action may comprise a confidence evaluation. For example, the closer the results of the concordance analysis is to 0 (for the concordance decision) or 1 (for the discordance decision), the higher the confidence evaluation is.

In one embodiment, the relationship matrix $RM_{\_CTA \rightarrow SPECT}$ applied to perform the concordance analysis at step 108 may be updated with patient-specific vessel territories. Relationship matrix $RM_{\_CTA \rightarrow SPECT}$ is updated using TERR_CORRESP and SPECT_SEGM_NEIGHB matrices.

The TERR_CORRESP matrix is an n×3 matrix, where n is the number of segments in the functional (SPECT) model and each column corresponds to a territory (e.g., LAX, LCx, RCA). The values in the TERR_CORESP matrix represent the contribution of the arteries of each territory to each SPECT SEGMENT in percentages.

Figure 10:
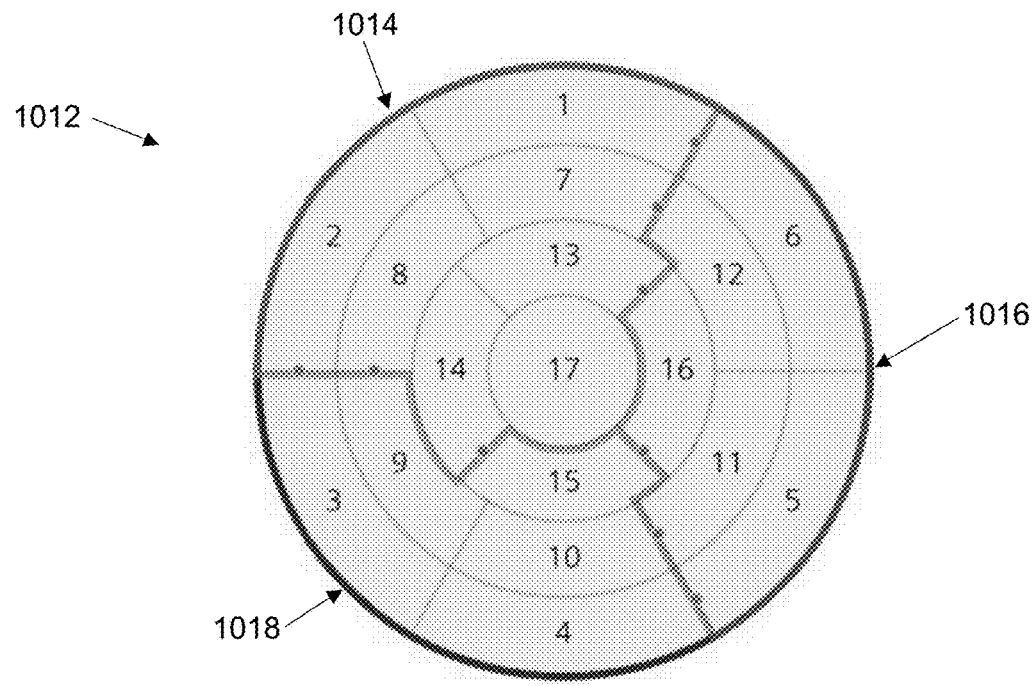
FIG. 10 shows an exemplary TERR_CORRESP matrix for a standard definition of a 17-segment SPECT model, in accordance with one or more embodiments.

FIG. 10 shows an exemplary TERR_CORRESP matrix 1000 for a standard definition of a 17-segment SPECT model 1012, in accordance with one or more embodiments. Matrix 1000 is shown as having rows 1010 corresponding to the 17 segments of the SPECT model 1012, column 1002 identifying a number associated with the SPECT segment according to SPECT model 1012, and columns 1004-1008 respectively identifying the contribution of the LAD, LCx, and RCA to the segment for the corresponding row 1010 as a percentage. In SPECT model 1012, territory 1014 corresponds to the LAD, territory 1016 corresponds to the LCx, and territory 1018 corresponds to the RCA. As shown in FIG. 10, in accordance with the standard definition of SPECT model 1012, each segment is assigned to a single territory and, hence, each row 1010 of matrix 1000 is assigned 100% to one territory and 0% in the remaining two territories in columns 1002-1006.

Figure 11:
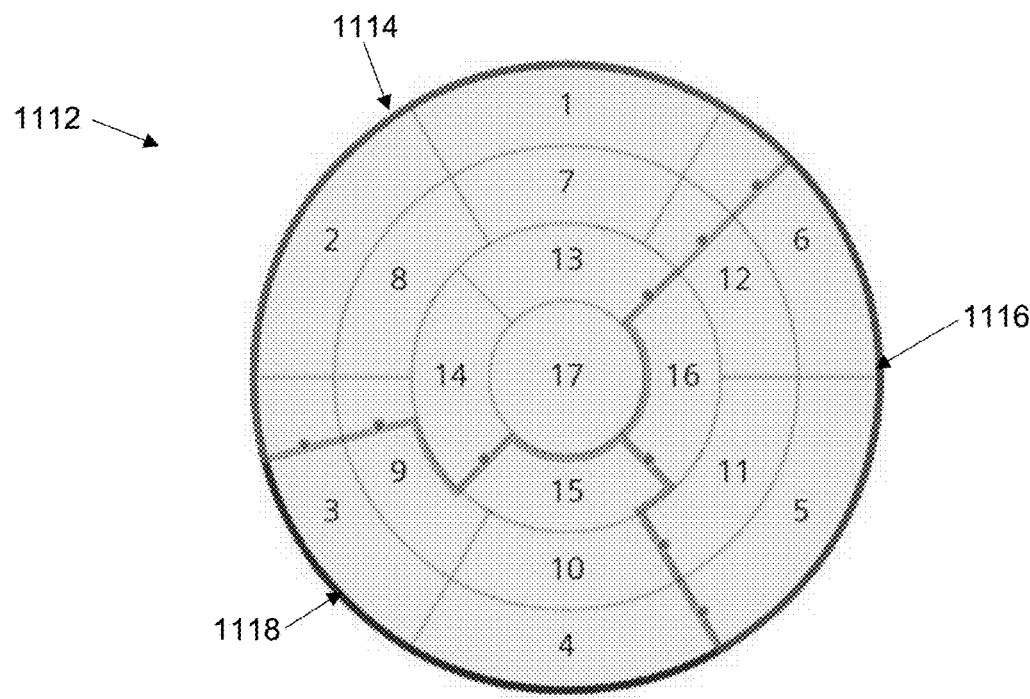
FIG. 11 shows an exemplary TERR_CORRESP matrix for a patient-specific definition of a 17-segment SPECT model, in accordance with one or more embodiments.

FIG. 11 shows an exemplary TERR_CORRESP matrix 1100 for a patient-specific definition of a 17-segment SPECT model 1112, in accordance with one or more embodiments. Matrix 1100 is shown as having rows 1110 corresponding to the 17 segments of the SPECT model 1112, column 1102 identifying a number associated with the SPECT segment according to SPECT model 1112, and columns 1104-1108 respectively identifying the contribution of the LAD, LCx, and RCA to the segment for the corresponding row 1110 as a percentage. In SPECT model 1112, territory 1114 corresponds to the LAD, territory 1116 corresponds to the LCx, and territory 1118 corresponds to the RCA. As shown in FIG. 11, in accordance with the patient-specific definition of SPECT model 1112, the LAD territory 1114 extends into segments 6 and 12 (originally contributing 100% to the LCx territory, as shown in FIG. 10) and segments 3 and 9 (originally contributing 100% to the RCA territory, as shown in FIG. 10). Accordingly, TERR_CORRESP matrix 1100 is defined such that segments 3 and 9 contribute 24% to the LAD territory and 76% to the RCA territory and segments 6 and 12 contribute 24% to the LAD territory and 76% to the LCx territory. Different approached may be followed to define the values in TERR_CORRESP matrix 1100. In one embodiment, an interactive GUI (graphical user interface) may be employed where a user (e.g., physician or other clinician) can manually adapt the territories starting from, e.g., the standard definition of the territories (in FIG. 10). In another embodiment, if medical images of the patient are available, the values may be automatically defined by analyzing the relative position between the epicardial arteries and the SPECT standard segments.

The SPECT_SEGM_NEIGHB matrix is an n×3 matrix, where n is the number of segments in the functional (SPECT) model and each column corresponds to a territory (e.g., LAX, LCx, RCA). FIG. 12 shows an exemplary SPECT_SEGM_NEIGHB matrix 1200, in accordance with one or more embodiments. Matrix 1200 is shown as having rows 1210 corresponding to the 17 segments of the SPECT model, column 1202 identifying a number associated with the SPECT segment, and columns 1204-1208 identifying neighboring segments associated with a different territory within a ring level of the SPECT model. SPECT_SEGM_NEIGHB matrix 1200 is constant and is not adapted in a patient-specific manner. The role of SPECT_SEGM_NEIGHB matrix 1200 is to store, for each SPECT segment, information relating to neighboring segments and their corresponding territories in the standard definition of the SPECT model (in FIG. 10). In SPECT_SEGM_NEIGHB matrix 1200, the first row of rows 1210, corresponding to segment 1 in the SPECT model, has a value of 1 in LAD column 1204 since segment 1 is part of the LAD territory, has a value of 6 in LCx column 1206 because segment 6 is a neighbor of segment 1 and is part of the LCx territory, and has a value of −1 in RCA column 1208 because segment 1 has no neighboring segments in the RCA territory. Segment 2 is a neighbor segment of segment 1, however since it is part of the same LAD territory, it is not identified in matrix 1200.

To update relationship matrix $RM_{CTA \rightarrow SPECT}$, for each respective SPECT segment, values in rows of the SPECT_SEGM_NEIGHB matrix corresponding to the respective SPECT segment are identified. The columns of the relationship matrix $RM_{CTA \rightarrow SPECT}$ corresponding to the values identified in the SPECT_SEGM_NEIGHB matrix are extracted and the extracted column vectors are weighted by the values in the TERR_CORREP matrix for the respective SPECT segment and corresponding territories. The weighted column vectors are added up to determine the values in the updated relationship matrix. The relationship matrix $RM_{CTA \rightarrow SPECT}$ may be updated before or after being normalized.

Pseudo-code for updating relationship matrix $RM_{CTA \rightarrow SPECT}$ is as follows:

```
for each SPECT segment s:
   if SPECT_neighbors[s][LAD] ≥ 0:
      RM_col_index = SPECT_SEGM_NEIGHB[s][LAD]
      LAD_v = TERR_CORRESP[s][LAD] * (column RM_col_index
of RM_MATRIX_orig)
   if SPECT_neighbors[s][LCx] ≥ 0:
      RM_col_index = SPECT_SEGM_NEIGHB[s][LCx]
      LCx_v = TERR_CORRESP[s][LCx] * (column RM_col_index
of RM_MATRIX_orig)
   if SPECT_neighbors[s][RCA] ≥ 0:
      RM_col_index = SPECT_SEGM_NEIGHB[s][LCx]
      RCA_v = TERR_CORRESP[s][LCx] * (column RM_col_index
of RM_MATRIX_orig)
      column s of RM_MATRIX = LAD_v + LCx_v + RCA_v
```

The algorithm for updating relationship matrix $RM_{CTA \rightarrow SPECT}$ was tested to evaluate the performance of the concordance analysis for cases where patient-specific vessel territories were used. The tests were run in all SPECT configurations (i.e., 16, 17, and 18 segment models) and the results did not different significantly.

Figure 13:
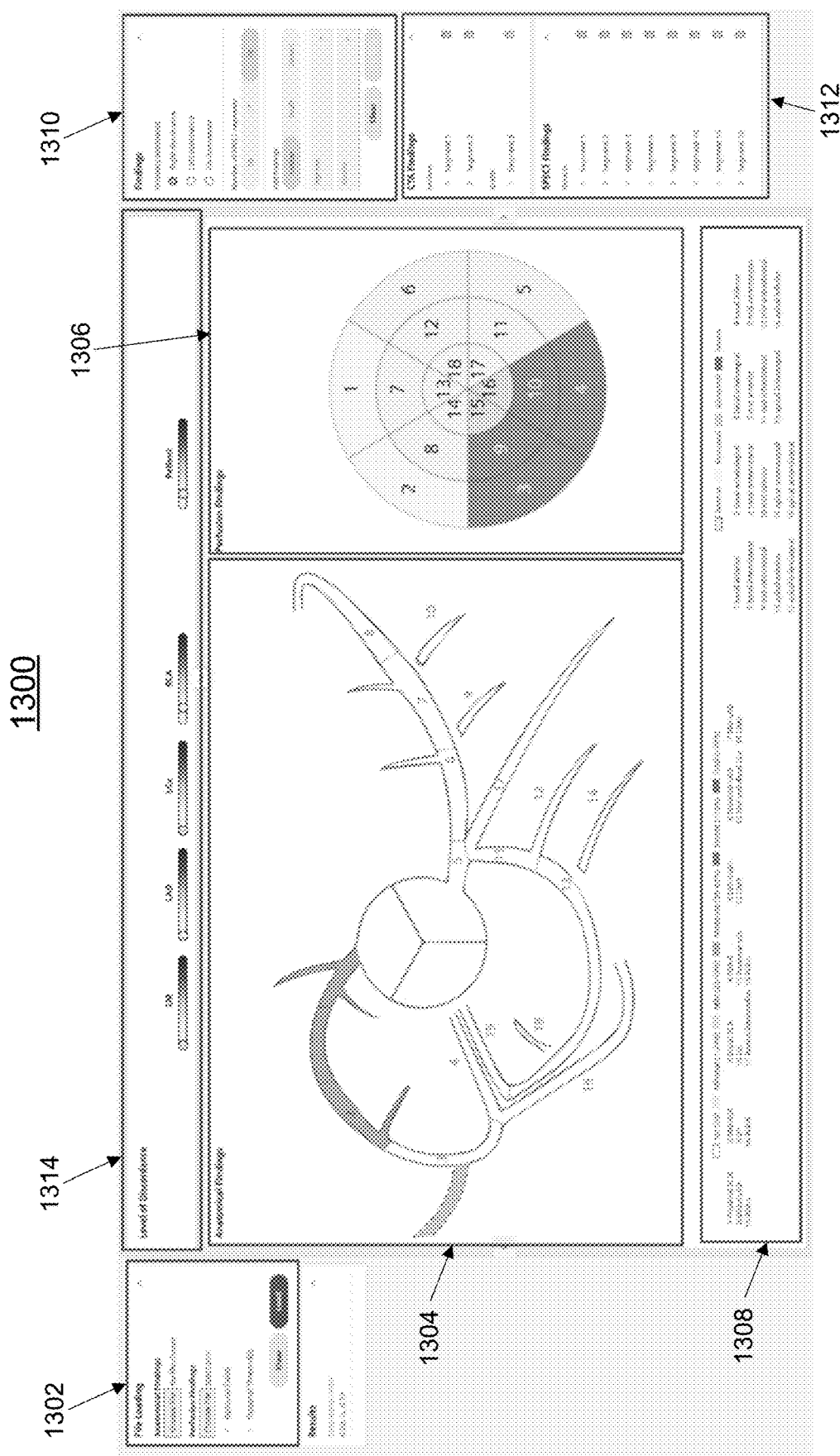
FIG. 13 shows a user interface enabling user interaction for performing a concordance analysis between results of medical assessments, in accordance with one or more embodiments.

FIG. 13 shows a user interface 1300 enabling user interaction for performing a concordance analysis between results of medical assessments, in accordance with one or more embodiments. The concordance analysis may be performed according to method 100 of FIG. 1. User interface 1300 enables a user (e.g., a clinician) to load, add, or remove results of medical assessments for performing the concordance analysis. The results of the concordance analysis are computed automatically after every change made by the user via user interface 1300.

User interface 1300 is split into a file loading area 1302, a CTA findings area 1304, a SPECT findings area 1306, a legend area 1308, a findings area 1310, a findings list area 1312, and a results area 1314. Each area 1302-1314 has a different role in the user interface.

File loading area 1302 is used for loading preexisting cases. File loading area 1302 comprises two input fields: one for loading CTA findings and one for loading SPECT findings. After selecting the files, the user can load the findings by clicking the "load" button. The user can also clear the loaded findings by clicking the "clear" button.

CTA findings area 1304 presents the CTA (or anatomical) findings loaded or added by the user (via file loading area 1302). The user can add or change the severity of a finding by right clicking a segment and, selecting a severity of the segment from a pop-up menu.

SPECT findings area 1306 presents the SPECT (or perfusion) findings loaded or added by the user (via file loading area 1302). Similar to CTA findings area 1304, the user can add or change the severity of a finding in SPECT findings area 1306 by right clicking a segment and, selecting a severity of the segment from a pop-up menu.

Legend area 1308 presents legends for facilitating user interpretation of CTA findings area 1306 and SPECT findings area 1306. For SPECT findings area 1306, legend area 1308 will change to reflect the selected number of segments.

Findings area 1310 enables the user to change different inputs for performing the concordance analysis. For example, the user can change the number of SPECT segments, the type of coronary dominance via findings area 1310. The user can also add findings for a lesion (e.g., stenosis), graft or defect by defining the segment and severity.

Findings list area 1312 enables the user to view and edit the existing findings in a list view.

Results area 1314 presents results of the concordance analysis in the form of gradient bars. Results area 1314 shows gradient bars indicating the level of discordance (or concordance) for the LAD, LCx, and RCA territories of the coronary artery, as well as a gradient bar indicating the patient-level discordance. For every change made by the user interacting with user interface 1300, the concordance analysis will be performed (e.g., according to method 100 of FIG. 1) and the results in results area 1314 are updated. In each gradient bar, the circle being closer to the left side indicates a higher level of concordance between the CTA findings and the SPECT findings while the circle being closer to the right side indicates a higher level of discordance between the CTA findings and the SPECT findings.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 14:
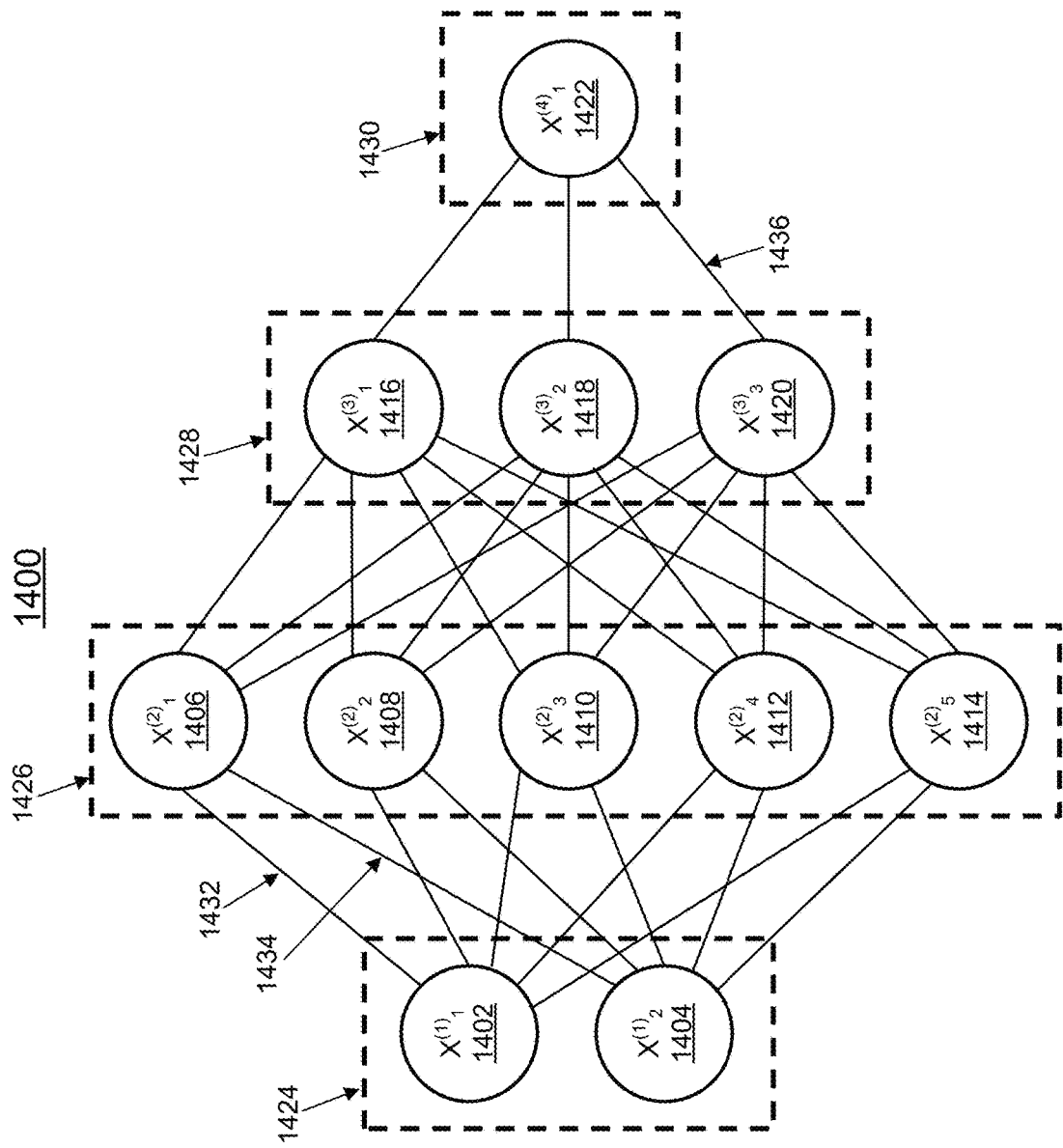
FIG. 14 shows an exemplary artificial neural network that may be used to implement one or more embodiments.

FIG. 14 shows an embodiment of an artificial neural network 1400, in accordance with one or more embodiments. Alternative terms for "artificial neural network" are "neural network", "artificial neural net" or "neural net". Machine learning networks described herein may be implemented using artificial neural network 1400.

The artificial neural network 1400 comprises nodes 1402-1422 and edges 1432, 1434, ..., 1436, wherein each edge 1432, 1434, ..., 1436 is a directed connection from a first node 1402-1422 to a second node 1402-1422. In general, the first node 1402-1422 and the second node 1402-1422 are different nodes 1402-1422, it is also possible that the first node 1402-1422 and the second node 1402-1422 are identical. For example, in FIG. 14, the edge 1432 is a directed connection from the node 1402 to the node 1406, and the edge 1434 is a directed connection from the node 1404 to the node 1406. An edge 1432, 1434, ..., 1436 from a first node 1402-1422 to a second node 1402-1422 is also denoted as "ingoing edge" for the second node 1402-1422 and as "outgoing edge" for the first node 1402-1422.

In this embodiment, the nodes 1402-1422 of the artificial neural network 1400 can be arranged in layers 1424-1430, wherein the layers can comprise an intrinsic order introduced by the edges 1432, 1434, ..., 1436 between the nodes 1402-1422. In particular, edges 1432, 1434, ..., 1436 can exist only between neighboring layers of nodes. In the embodiment shown in FIG. 14, there is an input layer 1424 comprising only nodes 1402 and 1404 without an incoming edge, an output layer 1430 comprising only node 1422 without outgoing edges, and hidden layers 1426, 1428 in-between the input layer 1424 and the output layer 1430. In general, the number of hidden layers 1426, 1428 can be chosen arbitrarily. The number of nodes 1402 and 1404 within the input layer 1424 usually relates to the number of input values of the neural network 1400, and the number of nodes 1422 within the output layer 1430 usually relates to the number of output values of the neural network 1400.

In particular, a (real) number can be assigned as a value to every node 1402-1422 of the neural network 1400. Here, $x^{(n)}_i$ denotes the value of the i-th node 1402-1422 of the n-th layer 1424-1430. The values of the nodes 1402-1422 of the input layer 1424 are equivalent to the input values of the neural network 1400, the value of the node 1422 of the output layer 1430 is equivalent to the output value of the neural network 1400. Furthermore, each edge 1432, 1434, ..., 1436 can comprise a weight being a real number, in particular, the weight is a real number within the interval $[-1, 1]$ or within the interval $[0, 1]$. Here, $w^{(m,n)}_{i,j}$ denotes the weight of the edge between the i-th node 1402-1422 of the m-th layer 1424-1430 and the j-th node 1402-1422 of the n-th layer 1424-1430. Furthermore, the abbreviation $w^{(n)}_{i,j}$ is defined for the weight $w^{(n,n+1)}_{i,j}$.

In particular, to calculate the output values of the neural network 1400, the input values are propagated through the neural network. In particular, the values of the nodes 1402-1422 of the (n+1)-th layer 1424-1430 can be calculated based on the values of the nodes 1402-1422 of the n-th layer 1424-1430 by $$x_j^{(n+1)} = f(\Sigma x_i^{(n)} \cdot w_{i,j}^{(n)}).$$

Herein, the function $f$ is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 1424 are given by the input of the neural network 1400, wherein values of the first hidden layer 1426 can be calculated based on the values of the input layer 1424 of the neural network, wherein values of the second hidden layer 1428 can be calculated based in the values of the first hidden layer 1426, etc.

In order to set the values $w^{(m,n)}_{i,j}$ for the edges, the neural network 1400 has to be trained using training data. In particular, training data comprises training input data and training output data (denoted as $t_i$). For a training step, the neural network 1400 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 1400 (backpropagation algorithm). In particular, the weights are changed according to $$w'^{(n)}_{i,j} = w^{(n)}_{i,j} - \gamma \cdot \delta_j^{(n)} \cdot x_i^{(n)}$$

wherein γ is a learning rate, and the numbers $\delta^{(n)}_j$ can be recursively calculated as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)} = (x_k^{(n+1)} - t_j^{(n+1)}) \cdot f'(\Sigma_i x_i^{(n)} \cdot w_{i,j}^{(n)})$$

if the (n+1)-th layer is the output layer 1430, wherein $f'$ is the first derivative of the activation function, and $y^{(n+1)}_j$ is the comparison training value for the j-th node of the output layer 1430.

Figure 15:
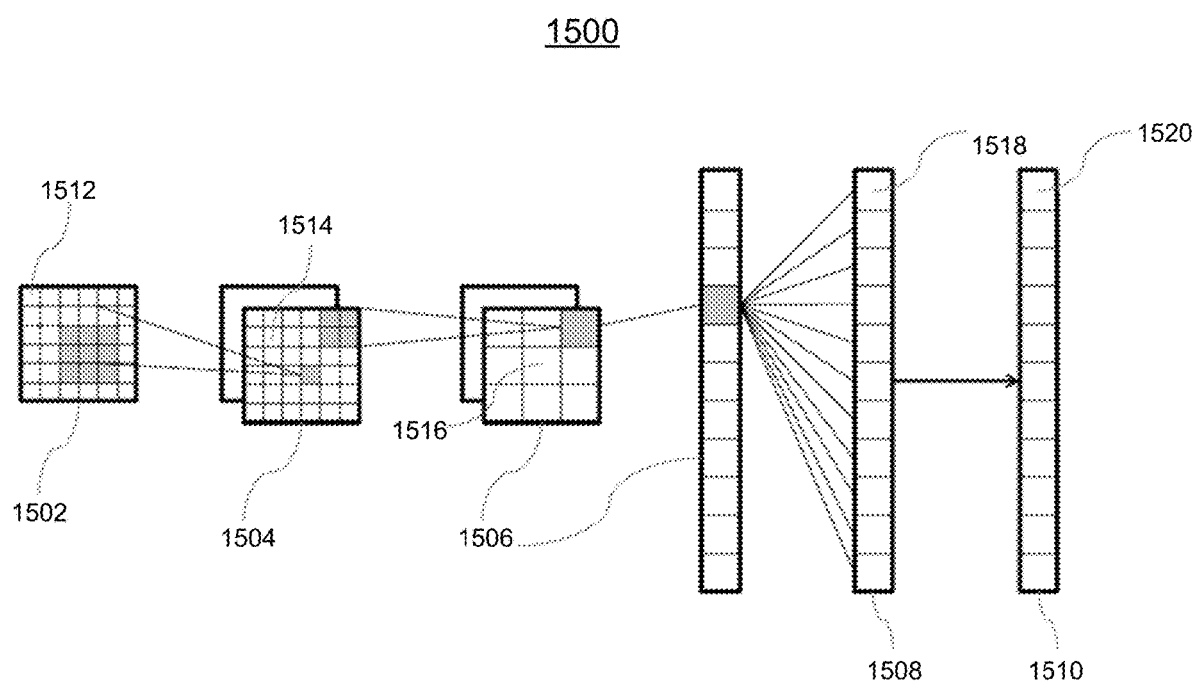
FIG. 15 shows a convolutional neural network that may be used to implement one or more embodiments.

FIG. 15 shows a convolutional neural network 1500, in accordance with one or more embodiments. Machine learning networks described herein may be implemented using convolutional neural network 1500.

In the embodiment shown in FIG. 15, the convolutional neural network comprises 1500 an input layer 1502, a convolutional layer 1504, a pooling layer 1506, a fully connected layer 1508, and an output layer 1510. Alternatively, the convolutional neural network 1500 can comprise several convolutional layers 1504, several pooling layers 1506, and several fully connected layers 1508, as well as other types of layers. The order of the layers can be chosen arbitrarily, usually fully connected layers 1508 are used as the last layers before the output layer 1510.

In particular, within a convolutional neural network 1500, the nodes 1512-1520 of one layer 1502-1510 can be considered to be arranged as a d-dimensional matrix or as a d-dimensional image. In particular, in the two-dimensional case the value of the node 1512-1520 indexed with i and j in the n-th layer 1502-1510 can be denoted as $x^{(n)}_{[i,j]}$. However, the arrangement of the nodes 1512-1520 of one layer 1502-1510 does not have an effect on the calculations executed within the convolutional neural network 1500 as such, since these are given solely by the structure and the weights of the edges.

In particular, a convolutional layer 1504 is characterized by the structure and the weights of the incoming edges forming a convolution operation based on a certain number of kernels. In particular, the structure and the weights of the incoming edges are chosen such that the values $x^{(n)}_k$ of the nodes 1514 of the convolutional layer 1504 are calculated as a convolution $x^{(n)}_k = K_k * x^{(n-1)}$ based on the values $x^{(n-1)}$ of the nodes 1512 of the preceding layer 1502, where the convolution * is defined in the two-dimensional case as $$x_k^{(n)}[i,j] = (K_k * x^{(n-1)})[i,j] = \Sigma_{i'}\Sigma_{j'} K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 1512-1518 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 1512-1520 in the respective layer 1502-1510. In particular, for a convolutional layer 1504, the number of nodes 1514 in the convolutional layer is equivalent to the number of nodes 1512 in the preceding layer 1502 multiplied with the number of kernels.

If the nodes 1512 of the preceding layer 1502 are arranged as a d-dimensional matrix, using a plurality of kernels can be interpreted as adding a further dimension (denoted as "depth" dimension), so that the nodes 1514 of the convolutional layer 1504 are arranged as a (d+1)-dimensional matrix. If the nodes 1512 of the preceding layer 1502 are already arranged as a (d+1)-dimensional matrix comprising a depth dimension, using a plurality of kernels can be interpreted as expanding along the depth dimension, so that the nodes 1514 of the convolutional layer 1504 are arranged also as a (d+1)-dimensional matrix, wherein the size of the (d+1)-dimensional matrix with respect to the depth dimension is by a factor of the number of kernels larger than in the preceding layer 1502.

The advantage of using convolutional layers 1504 is that spatially local correlation of the input data can exploited by enforcing a local connectivity pattern between nodes of adjacent layers, in particular by each node being connected to only a small region of the nodes of the preceding layer.

In embodiment shown in FIG. 15, the input layer 1502 comprises 36 nodes 1512, arranged as a two-dimensional 6×6 matrix. The convolutional layer 1504 comprises 72 nodes 1514, arranged as two two-dimensional 6×6 matrices, each of the two matrices being the result of a convolution of the values of the input layer with a kernel. Equivalently, the nodes 1514 of the convolutional layer 1504 can be interpreted as arranges as a three-dimensional 6×6×2 matrix, wherein the last dimension is the depth dimension.

A pooling layer 1506 can be characterized by the structure and the weights of the incoming edges and the activation function of its nodes 1516 forming a pooling operation based on a non-linear pooling function $f$. For example, in the two dimensional case the values $x^{(n)}$ of the nodes 1516 of the pooling layer 1506 can be calculated based on the values $x^{(n-1)}$ of the nodes 1514 of the preceding layer 1504 as $$x^{(n)}[i,j] = f(x^{(n-1)}[id_1, jd_2], \ldots, x^{(n-1)}[id_1 + d_1 - 1, jd_2 + d_2 - 1])$$

In other words, by using a pooling layer 1506, the number of nodes 1514, 1516 can be reduced, by replacing a number $d_1 \cdot d_2$ of neighboring nodes 1514 in the preceding layer 1504 with a single node 1516 being calculated as a function of the values of said number of neighboring nodes in the pooling layer. In particular, the pooling function $f$ can be the max-function, the average or the L2-Norm. In particular, for a pooling layer 1506 the weights of the incoming edges are fixed and are not modified by training.

The advantage of using a pooling layer 1506 is that the number of nodes 1514, 1516 and the number of parameters is reduced. This leads to the amount of computation in the network being reduced and to a control of overfitting.

In the embodiment shown in FIG. 15, the pooling layer 1506 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 1508 can be characterized by the fact that a majority, in particular, all edges between nodes 1516 of the previous layer 1506 and the nodes 1518 of the fully-connected layer 1508 are present, and wherein the weight of each of the edges can be adjusted individually.

In this embodiment, the nodes 1516 of the preceding layer 1506 of the fully-connected layer 1508 are displayed both as two-dimensional matrices, and additionally as non-related nodes (indicated as a line of nodes, wherein the number of nodes was reduced for a better presentability). In this embodiment, the number of nodes 1518 in the fully connected layer 1508 is equal to the number of nodes 1516 in the preceding layer 1506. Alternatively, the number of nodes 1516, 1518 can differ.

Furthermore, in this embodiment, the values of the nodes 1520 of the output layer 1510 are determined by applying the Softmax function onto the values of the nodes 1518 of the preceding layer 1508. By applying the Softmax function, the sum the values of all nodes 1520 of the output layer 1510 is 1, and all values of all nodes 1520 of the output layer are real numbers between 0 and 1.

A convolutional neural network 1500 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 1500 can be trained based on the backpropagation algorithm. For preventing overfitting, methods of regularization can be used, e.g. dropout of nodes 1512-1520, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1. Certain steps or functions of the methods and workflows described herein, including one or more of the steps or functions of FIG. 1, may be performed by a server or by another processor in a network-based cloud-computing system. Certain steps or functions of the methods and workflows described herein, including one or more of the steps of FIG. 1, may be performed by a client computer in a network-based cloud computing system. The steps or functions of the methods and workflows described herein, including one or more of the steps of FIG. 1, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 16:
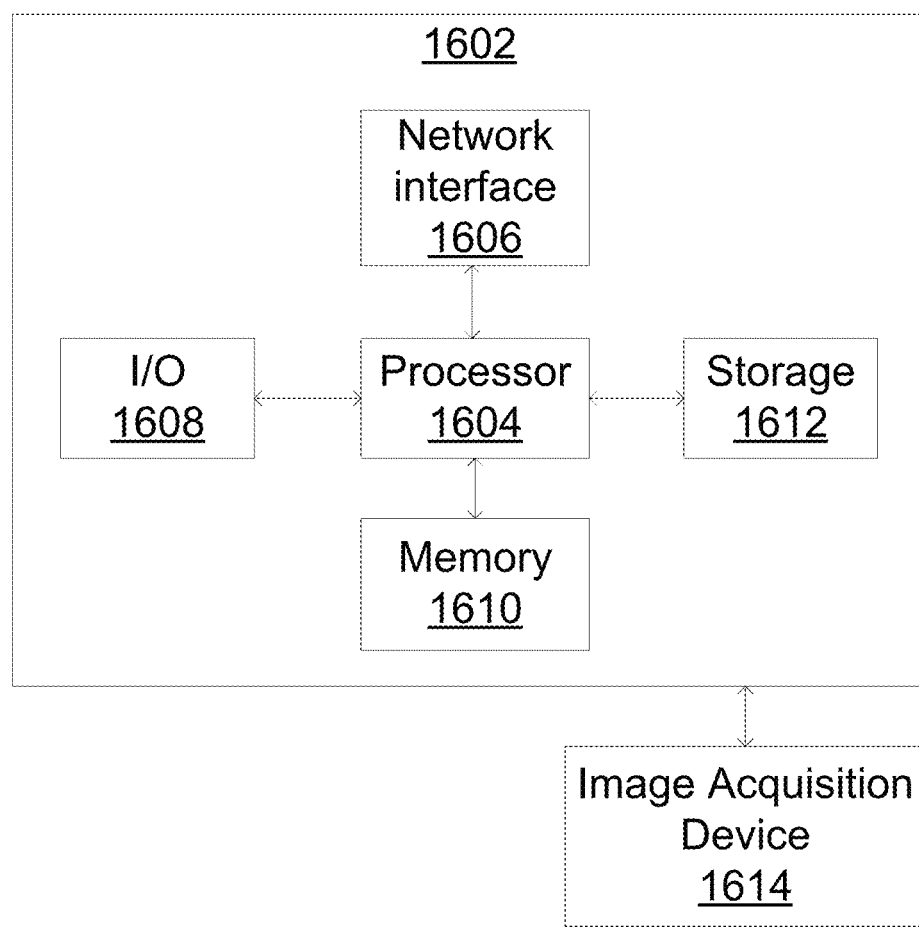
FIG. 16 shows a high-level block diagram of a computer that may be used to implement one or more embodiments.

A high-level block diagram of an example computer 1602 that may be used to implement systems, apparatus, and methods described herein is depicted in FIG. 16. Computer 1602 includes a processor 1604 operatively coupled to a data storage device 1612 and a memory 1610. Processor 1604 controls the overall operation of computer 1602 by executing computer program instructions that define such operations. The computer program instructions may be stored in data storage device 1612, or other computer readable medium, and loaded into memory 1610 when execution of the computer program instructions is desired. Thus, the method and workflow steps or functions of FIG. 1 can be defined by the computer program instructions stored in memory 1610 and/or data storage device 1612 and controlled by processor 1604 executing the computer program instructions. For example, the computer program instructions can be implemented as computer executable code programmed by one skilled in the art to perform the method and workflow steps or functions of FIG. 1. Accordingly, by executing the computer program instructions, the processor 1604 executes the method and workflow steps or functions of FIG. 1. Computer 1602 may also include one or more network interfaces 1606 for communicating with other devices via a network. Computer 1602 may also include one or more input/output devices 1608 that enable user interaction with computer 1602 (e.g., display, keyboard, mouse, speakers, buttons, etc.).

Processor 1604 may include both general and special purpose microprocessors, and may be the sole processor or one of multiple processors of computer 1602. Processor 1604 may include one or more central processing units (CPUs), for example. Processor 1604, data storage device 1612, and/or memory 1610 may include, be supplemented by, or incorporated in, one or more application-specific integrated circuits (ASICs) and/or one or more field programmable gate arrays (FPGAs).

Data storage device 1612 and memory 1610 each include a tangible non-transitory computer readable storage medium. Data storage device 1612, and memory 1610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1608 may include peripherals, such as a printer, scanner, display screen, etc. For example, input/output devices 1608 may include a display device such as a cathode ray tube (CRT) or liquid crystal display (LCD) monitor for displaying information to the user, a keyboard, and a pointing device such as a mouse or a trackball by which the user can provide input to computer 1602.

An image acquisition device 1614 can be connected to the computer 1602 to input image data (e.g., medical images) to the computer 1602. It is possible to implement the image acquisition device 1614 and the computer 1602 as one device. It is also possible that the image acquisition device 1614 and the computer 1602 communicate wirelessly through a network. In a possible embodiment, the computer 1602 can be located remotely with respect to the image acquisition device 1614.

Any or all of the systems and apparatus discussed herein may be implemented using one or more computers such as computer 1602.

One skilled in the art will recognize that an implementation of an actual computer or computer system may have other structures and may contain other components as well, and that FIG. 16 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
receiving results of a medical assessment of a first type for an anatomical object of a patient;
receiving results of a medical assessment of a second type for the anatomical object;
converting the results of the medical assessment of the first type to a hemodynamic measure;
performing a concordance analysis between the results of the medical assessment of the first type and the results of the medical assessment of the second type based on the hemodynamic measure; and
outputting results of the concordance analysis.

2. The computer-implemented method of claim 1, wherein the medical assessment of the first type is an anatomical assessment and the medical assessment of the second type is a functional assessment.

3. The computer-implemented method of claim 2, wherein the anatomical assessment is based on CTA (computed tomography angiography) and the functional assessment is based on SPECT (single-photon emission computerized tomography).

4. The computer-implemented method of claim 1, wherein converting the results of the medical assessment of the first type to a hemodynamic measure comprises:
for each respective segment of the anatomical object, determining a severity of the respective segment as a maximum of severities of the respective segment and parent segments of the respective segment.

5. The computer-implemented method of claim 1, wherein performing a concordance analysis between the results of the medical assessment of the first type and the results of the medical assessment of the second type based on the hemodynamic measure comprises:
determining a first concordance for each territory of the anatomical object by interrelating the hemodynamic measure to the medical assessment of the second type;
determining a second concordance for each territory of the anatomical object by interrelating the results of the medical assessment of the second type to the medical assessment of the first type; and
combining the first concordance and the second concordance to determine a final concordance for each territory of the anatomical object.

6. The computer-implemented method of claim 1, wherein performing a concordance analysis between the results of the medical assessment of the first type and the results of the medical assessment of the second type based on the hemodynamic measure comprises:
defining a relationship matrix based on a coronary dominance of the patient; and
performing the concordance analysis based on the defined relationship matrix.

7. The computer-implemented method of claim 1, wherein:
receiving results of a medical assessment of a first type for an anatomical object of a patient comprises:
generating the results of the medical assessment of the first type to include results for one or more additional segments; and
converting the results of the medical assessment of the first type to a hemodynamic measure comprises:
updating a dictionary to define a parent segment for each of the one or more additional segments, and
converting the results of the medical assessment of the first type to the hemodynamic measure based on the updated dictionary; and
performing a concordance analysis between the results of the medical assessment of the first type and the results of the medical assessment of the second type based on the hemodynamic measure comprises:
updating a relationship matrix for the one or more additional segments, and
performing the concordance analysis between the generated results of the medical assessment of the first type and the results of the medical assessment of the second type based on the updated relationship matrix and the updated dictionary.

8. The computer-implemented method of claim 1, wherein
receiving results of a medical assessment of a first type for an anatomical object of a patient comprises:
generating the results of the medical assessment of the first type to include results for one or more bypass graft segments;
converting the results of the medical assessment of the first type to a hemodynamic measure comprises:
updating a dictionary to define a parent segment for each of the one or more bypass graft segments, and
converting the results of the medical assessment of the first type to the hemodynamic measure based on the updated dictionary; and
performing a concordance analysis between the results of the medical assessment of the first type and the results of the medical assessment of the second type based on the hemodynamic measure comprises:
updating the measure of the second type by removing the one or more bypass graft segments from the hemodynamic measure; and
performing the concordance analysis between the generated results of the medical assessment of the first type and the results of the medical assessment of the second type based on the updated hemodynamic measure.

9. The computer-implemented method of claim 1, further comprising:
randomly varying an anatomical model of the anatomical object;
adding one or more stenoses to the randomly varied anatomical model;
determining one or more flow rates based on the randomly varied anatomical model with the one or more added stenoses;
determining one or more functional defects to each of a plurality of segments based on the one or more flow rates; and
adjusting a relationship matrix for performing the concordance analysis based on the one or more stenoses and the one or more functional defects.

10. The computer-implemented method of claim 1, wherein performing a concordance analysis between the results of the medical assessment of the first type and the results of the medical assessment of the second type based on the hemodynamic measure comprises performing the concordance analysis based on a relationship matrix and wherein the relationship matrix is updated based on 1) a first matrix representing a contribution of arteries of territories of the anatomical object to each segment of a functional model of the anatomical object and 2) a second matrix identifying, for each segment of the functional model, neighboring segments that are associated with a different territory within a ring level of the functional model.

11. An apparatus comprising:
means for receiving results of a medical assessment of a first type for an anatomical object of a patient;
means for receiving results of a medical assessment of a second type for the anatomical object;
means for converting the results of the medical assessment of the first type to a hemodynamic measure;
means for performing a concordance analysis between the results of the medical assessment of the first type and the results of the medical assessment of the second type based on the hemodynamic measure; and
means for outputting results of the concordance analysis.

12. The apparatus of claim 11, wherein the medical assessment of the first type is an anatomical assessment and the medical assessment of the second type is a functional assessment.

13. The apparatus of claim 12, wherein the anatomical assessment is based on CTA (computed tomography angiography) and the functional assessment is based on SPECT (single-photon emission computerized tomography).

14. The apparatus of claim 11, wherein the means for converting the results of the medical assessment of the first type to a hemodynamic measure comprises:
means for, for each respective segment of the anatomical object, determining a severity of the respective segment as a maximum of severities of the respective segment and parent segments of the respective segment.

15. The apparatus of claim 11, wherein the means for performing a concordance analysis between the results of the medical assessment of the first type and the results of the medical assessment of the second type based on the hemodynamic measure comprises:
means for determining a first concordance for each territory of the anatomical object by interrelating the hemodynamic measure to the medical assessment of the second type;
means for determining a second concordance for each territory of the anatomical object by interrelating the results of the medical assessment of the second type to the medical assessment of the first type; and
means for combining the first concordance and the second concordance to determine a final concordance for each territory of the anatomical object.

16. A non-transitory computer readable medium storing computer program instructions, the computer program instructions when executed by a processor cause the processor to perform operations comprising:
receiving results of a medical assessment of a first type for an anatomical object of a patient;
receiving results of a medical assessment of a second type for the anatomical object;
converting the results of the medical assessment of the first type to a hemodynamic measure;
performing a concordance analysis between the results of the medical assessment of the first type and the results of the medical assessment of the second type based on the hemodynamic measure; and
outputting results of the concordance analysis.

17. The non-transitory computer readable medium of claim 16, wherein performing a concordance analysis between the results of the medical assessment of the first type and the results of the medical assessment of the second type based on the hemodynamic measure comprises:
defining a relationship matrix based on a coronary dominance of the patient; and
performing the concordance analysis based on the defined relationship matrix.

18. The non-transitory computer readable medium of claim 16, wherein:
receiving results of a medical assessment of a first type for an anatomical object of a patient comprises:
generating the results of the medical assessment of the first type to include results for one or more additional segments; and
converting the results of the medical assessment of the first type to a hemodynamic measure comprises:
updating a dictionary to define a parent segment for each of the one or more additional segments, and converting the results of the medical assessment of the first type to the hemodynamic measure based on the updated dictionary; and
performing a concordance analysis between the results of the medical assessment of the first type and the results of the medical assessment of the second type based on the hemodynamic measure comprises:
updating a relationship matrix for the one or more additional segments, and
performing the concordance analysis between the generated results of the medical assessment of the first type and the results of the medical assessment of the second type based on the updated relationship matrix and the updated dictionary.

19. The non-transitory computer readable medium of claim 16, wherein
receiving results of a medical assessment of a first type for an anatomical object of a patient comprises:
generating the results of the medical assessment of the first type to include results for one or more bypass graft segments;
converting the results of the medical assessment of the first type to a hemodynamic measure comprises:
updating a dictionary to define a parent segment for each of the one or more bypass graft segments, and
converting the results of the medical assessment of the first type to the hemodynamic measure based on the updated dictionary; and
performing a concordance analysis between the results of the medical assessment of the first type and the results of the medical assessment of the second type based on the hemodynamic measure comprises:
updating the hemodynamic measure by removing the one or more bypass graft segments from the hemodynamic measure; and
performing the concordance analysis between the generated results of the medical assessment of the first type and the results of the medical assessment of the second type based on the updated hemodynamic measure.

20. The non-transitory computer readable medium of claim 16, the operations further comprising:
randomly varying an anatomical model of the anatomical object;
adding one or more stenoses to the randomly varied anatomical model;
determining one or more flow rates based on the randomly varied anatomical model with the one or more added stenoses;
determining one or more functional defects to each of a plurality of segments based on the one or more flow rates; and
adjusting a relationship matrix for performing the concordance analysis based on the one or more stenoses and the one or more functional defects.

* * * * *